(12) United States Patent
Elisseeff et al.

(10) Patent No.: US 8,673,333 B2
(45) Date of Patent: Mar. 18, 2014

(54) CROSS-LINKED POLYMER MATRICES, AND METHODS OF MAKING AND USING SAME

(75) Inventors: Jennifer Elisseeff, Baltimore, MD (US); Rocky S. Tuan, Bethesda, MD (US); Qiang Li, Baltimore, MD (US); Dongan Wang, Singapore (SG); Ronald Paul Silverman, Baltimore, MD (US)

(73) Assignees: The Johns Hopkins University, Baltimore, MD (US); University of Maryland, Baltimore, Baltimore, MD (US); The United States of America, as represented by the Secretary, Department of Health & Human Services, Washington, DC (US)

( * ) Notice: Subject to any disclaimer, the term of this patent is extended or adjusted under 35 U.S.C. 154(b) by 493 days.

(21) Appl. No.: 11/470,164

(22) Filed: Sep. 5, 2006

(65) Prior Publication Data

US 2007/0098675 A1 May 3, 2007

Related U.S. Application Data

(63) Continuation of application No. 11/314,659, filed on Dec. 20, 2005, now abandoned, which is a continuation of application No. 11/090,362, filed on Mar. 25, 2005, now abandoned, which is a continuation of application No. PCT/US03/30532, filed on Sep. 25, 2003.

(60) Provisional application No. 60/413,152, filed on Sep. 25, 2002.

(51) Int. Cl.
*A61F 2/00* (2006.01)
*C08B 15/00* (2006.01)

(52) U.S. Cl.
CPC .................................. *C08B 15/005* (2013.01)
USPC ........................................................ 424/423

(58) Field of Classification Search
None
See application file for complete search history.

(56) References Cited

U.S. PATENT DOCUMENTS

| | | | |
|---|---|---|---|
| 4,678,468 | A | 7/1987 | Hiroyoshi |
| 5,017,229 | A | 5/1991 | Burns et al. |
| 5,310,881 | A | 5/1994 | Sakurai et al. |
| 5,344,459 | A | 9/1994 | Swartz |
| 5,410,016 | A | 4/1995 | Hubbell et al. |

(Continued)

FOREIGN PATENT DOCUMENTS

| | | |
|---|---|---|
| EP | 0 656 214 A1 | 6/1995 |
| EP | 0 693 499 A1 | 1/1996 |

(Continued)

OTHER PUBLICATIONS

Qiang et al., "Photocrosslinkable polysaccharides based on chondroitin sulfate" J. Biomed. Mat. Res., 2004, 68A(1), pp. 2833.*

(Continued)

*Primary Examiner* — Brian Gulledge
(74) *Attorney, Agent, or Firm* — Edwards Wildman Palmer LLP; Peter F. Corless

(57) ABSTRACT

Functionalized chondroitin sulfate, cross-linked polymer matrices comprising functionalized chondroitin sulfate, and methods of making and using the same are provided. Such polymer matrices may be used for tissue engineering, reconstructing cartilage, and the like. Kits are also provided for detection of cartilage degrading enzymes.

18 Claims, 14 Drawing Sheets

(56) References Cited

U.S. PATENT DOCUMENTS

| | | | |
|---|---|---|---|
| 5,462,976 | A | 10/1995 | Matsuda et al. |
| 5,510,418 | A | 4/1996 | Rhee et al. |
| 5,573,934 | A | 11/1996 | Hubbell et al. |
| 5,681,353 | A | 10/1997 | Li et al. |
| 5,700,848 | A | 12/1997 | Soon-Shiong et al. |
| 5,733,562 | A | 3/1998 | Lee |
| 5,749,968 | A | 5/1998 | Melanson et al. |
| 5,763,504 | A * | 6/1998 | Matsuda et al. ............... 522/87 |
| 5,811,094 | A | 9/1998 | Caplan et al. |
| 5,834,274 | A | 11/1998 | Hubbell et al. |
| 5,837,747 | A | 11/1998 | Soon-Shiong et al. |
| 5,858,746 | A | 1/1999 | Hubbell et al. |
| 5,986,043 | A | 11/1999 | Hubbell et al. |
| 6,060,582 | A | 5/2000 | Hubbell et al. |
| 6,129,761 | A | 10/2000 | Hubbell |
| 6,132,468 | A | 10/2000 | Mansmann |
| 6,224,893 | B1 | 5/2001 | Langer et al. |
| 6,376,742 | B1 | 4/2002 | Zdrahala et al. |
| 6,410,044 | B1 | 6/2002 | Chudzik et al. |
| 6,468,520 | B1 | 10/2002 | Rowe et al. |
| 6,602,294 | B1 | 8/2003 | Sittinger et al. |
| 6,602,975 | B2 | 8/2003 | Hubbell et al. |
| 6,629,997 | B2 | 10/2003 | Mansmann |
| 6,632,246 | B1 | 10/2003 | Simon et al. |
| 6,632,446 | B1 | 10/2003 | Hubbell et al. |
| 6,639,014 | B2 | 10/2003 | Pathak et al. |
| 6,699,471 | B2 | 3/2004 | Radice et al. |
| 6,712,822 | B2 | 3/2004 | Re et al. |
| 6,713,085 | B2 | 3/2004 | Geistlich et al. |
| 6,723,709 | B1 | 4/2004 | Pressato et al. |
| 2002/0165337 | A1 * | 11/2002 | Wallace et al. ............... 528/373 |

FOREIGN PATENT DOCUMENTS

| | | |
|---|---|---|
| EP | 1 172 386 B1 A1 | 1/2002 |
| JP | 2002-509538 | 3/2002 |
| JP | 2008-301903 A | 12/2008 |
| WO | 91/15252 A1 | 10/1991 |
| WO | WO-99/01143 | 1/1999 |
| WO | 00/55967 A1 | 9/2000 |
| WO | WO 2004/029137 * | 4/2004 |

OTHER PUBLICATIONS

Wang et al., "Multifunctional chondroitin sulphate for cartilage tissue-biomaterial integration", Nature Material, 2006, 6(5), pp. 385-392.*

Qiang et al., J. Biomed. Mat. Res., 2004. 68A(1), pp. 28-33.*

Elisseeff et al., Proc. Nat. Acad. Sci., USA, 1999, 96(6), pp. 3104-3107.* van Dijk-Wolthuis et al., Macromolecules, 1995, 28(18), pp. 6317-6322.*

Office Action (Notice of Final Rejection) mailed Sep. 10, 2010, in corresponding Japanese Patent Application No. 2004-539986 (with English Translation).

Kojima et al., "Synthesis of 4-(Methacryloyloxy)butyl Chondroitinesulfate and Enzyme Degradation of its Copolymer with Acrylamide", Journal of the Chemical Society of Japan, 1986, No. 9, pp. 1260-1262. (Japanese with English Abstract, and English Translation).

Almqvist et al., "Culture of chondrocytes in alginate surrounded by fibrin gel: characteristics of the cells over a period of eight weeks", Annals of the Rheumatic Diseases, British Medical Association, vol. 60, No. 8, pp. 781-790 (Aug. 2001).

European Search Report mailed Dec. 6, 2006, in corresponding European Patent Application No. 03781299.7.

* cited by examiner

CROSS-LINKED POLYMER MATRICES, AND METHODS OF MAKING AND USING SAME

CROSS REFERENCE TO RELATED APPLICATIONS

This application is a continuation of U.S. patent application Ser. No. 11/314,658, filed Dec. 20, 2005, now abandoned, which is a continuation of U.S. patent application Ser. No. 11/090,362, filed Mar. 25, 2005, now abandoned, which is a continuation of PCT/US2003/030532, filed Sep. 25, 2003, which claims the benefit of U.S. Provisional Patent Application No. 60/413,152, filed Sep. 25, 2002. The disclosures of these applications are incorporated herein by reference in their entirety.

INTRODUCTION

Proteoglycans are constituents of the extracellular matrix (CM) that may play key roles in a number of biological processes. These biomacromolecules may contribute to the functionality of extracellular networks. For example, proteoglycans may have roles in regulating the assembly of connective tissue matrices, in the binding of growth factors to either accentuate or inhibit this activity, and in the control of cell proliferation by direct or indirect interaction with tyrosine kinase receptors. These biological functions may be useful in creating biomaterial scaffolds. For example, a synthetic ECM that is bioactive and/or bioresponsive may have applications in drug delivery and tissue engineering.

Naturally derived biopolymers often have useful biological properties but lack the structural or functional characteristics required for biomedical applications. For example, cartilage tissue covers the surface of bone in articulating joints and provides structural integrity for tissues such as the ear and nose. Type II collagen and proteoglycans, including aggrecan, are the main components of the cartilage ECM and are responsible for the tissue's impressive compressive and tensile strength.

Chondroitin sulfate (CS) is a biopolymer that can form the "arms" of the aggrecan molecule, and forms a major component of cartilage ECM. Chondroitin sulfate may also have the ability to reduce pain and improve joint function in articular disease.

Cross-linked polymeric biomaterials are used extensively in numerous biomedical applications including coatings for medical devices, structural artificial implants, and drug delivery vehicles. Polymer networks may be formed, for example, by crosslinking water soluble polymer solutions to form a water insoluble polymer network. Mechanical and structural properties may be manipulated by modification of the crosslinking density which controls network pore size, water content, and mechanical properties.

Cross-linked polymers, matrices or gels may be used for tissue engineering due in part to their ability to efficiently encapsulate cells. In some cases, cross-linked polymers or gels may have a high, tissue-like water content which may allow nutrient and waste transport. A cross-linked polymer matrix that is biocompatible, or optionally, biodegradable, may be also be useful, for example, for detecting degeneration of cartilage in joints. Past work has shown that there may be a correlation between a gene mutation causing shortened G3 domain in aggrecan, and subsequent reduction in associated chondroitin sulfate, with a predisposition for intervertebral disc (IVD) degeneration. Degeneration of the IVD is a significant clinical problem associated with low back pain and development of lumbar disc rupture. An effective therapy is needed that will replace IVD mechanical and structural function while promoting biological repair and regeneration.

SUMMARY OF INVENTION

In part, the present disclosure provides for a composition comprising at least one monomeric unit of chondroitin sulfate functionalized by at least one polymerizable moiety. In some embodiments, the composition comprises at least ten monomeric units of functionalized, or at least 100 monomeric units of functionalized chondroitin sulfate, or at least 1000 or more units of functionalized chondroitin sulfate.

In another embodiment, at least one of the monomeric units of chondroitin sulfate is conjugated to at least one polymerizable moiety. The polymerizable moiety may be selected, for example, from methacrylates, ethacrylates, itaconates, acrylamides, and aldehydes. The monomeric unit of chondroitin sulfate may functionalized through one or more thio, aldehyde or carboxylic acid moieties on said monomeric unit.

In some embodiments, compositions of the present invention are provided that may be represent by Formula I, II or III:

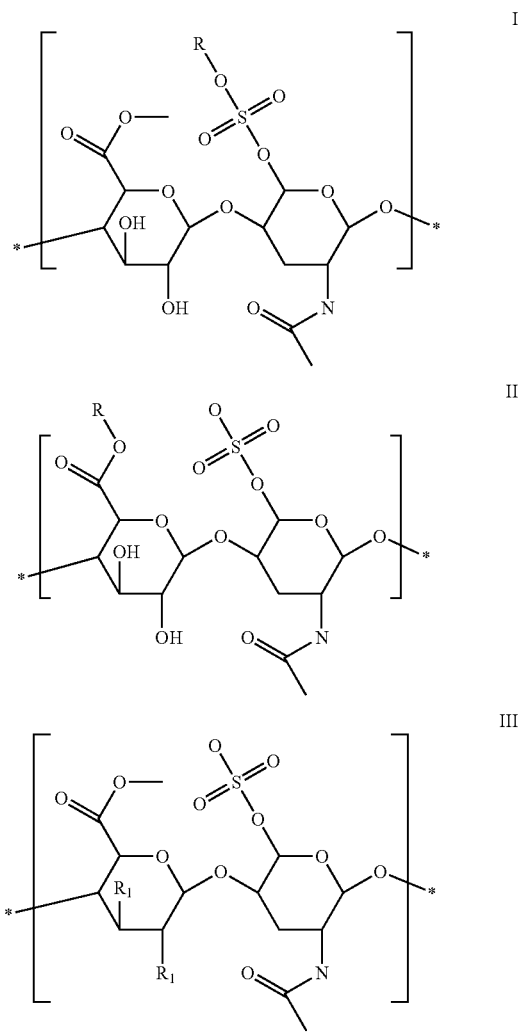

wherein R is alkenyl, and $R_1$ is independently selected from aldehyde or alcohol, wherein at least one $R_1$ is aldehyde. In some embodiments, R is:

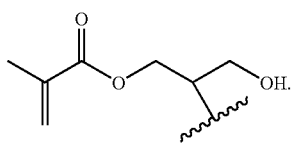 [SMILES: *C(CO)COC(=O)C(=C)C]

Further, the functionalized chondrotin sulfate compositions may comprise at least one monomeric unit of a biocompatible polymer. In some embodiments, the biocompatible polymer is polyethylene glycol polymer, such as acrylate-polyethylene-acrylate.

The present disclosure also provides for a composition comprising a cross linked polymer matrix, wherein the cross-linked polymer matrix comprises at least one monomeric unit of functionalized chrondoitin sulfate. In some embodiments, one or more monomeric units of chrondoitin sulfate is functionalized with an alkenyl moiety, such as methacrylate. In other embodiments, on or more monomeric units of chrondoitin sulfate is functionalized with an aldehyde moiety. Cross-linked polymer matrices of the present disclosure may be a hydrogel.

Compositions of the present disclosure may further comprise a detectable agent, such as a dye or fluorescent agent, or a biologically active agent, such as a chondrocyte or mesenchymal stem cell.

In some embodiments, cross-linked polymer matrices of the present disclosure further comprise at least one monomeric unit of a biocompatible polymer or a compound comprising an amine moiety, such as a protein, for example, albumin.

In some embodiments, a cross-linked polymer matrix comprises at least about 75%, at least about 50%, at least about 25%, or less than about 25% of biocompatible polymer by weight.

A method of producing a functionalized saccharide moiety, such as, for example, a monomeric unit of chondroitin sulfate, is further provided, wherein the method comprises: providing a solution comprising a compound comprising at least one saccharide unit, and a compound comprising an alkylene moiety, for example methacrylic anhydride, acryloyl chloride, or glycidyl methacrylate; and stirring the solution for at least 10 days. In some embodiments, the solution can be stirred for at least 15 days. The solution may comprise a polar solvent, for example, a hydrophilic solvent.

A method of producing a composition comprising a cross-linked polymer matrix is also provided, wherein the method includes providing a polymer comprising at least one monomeric unit of functionalized chondroitin sulfate; and exposing the polymer to at least one polymerizing initiator, thereby producing a cross-linked matrix. Polymerizing initiators may include electromagnetic radiation, dye agents, thermal initiators, redox initiators, and chemical initiators.

An additional method of making a composition which comprises a cross-linked polymer matrix is also provided wherein the method includes providing a polymer comprising at least one monomeric unit of chondroitin sulfate functionalized with at least one aldehyde; and providing a compound comprising an amine moiety; thereby producing a cross-linked matrix.

A further method is provided for restoring a smooth articulation surface to a skeletal joint in need thereof, comprising: administering a composition comprising at least one monomeric unit of functionalized chondroitin sulfate to an articular surface of bone in a joint. In some embodiments, the method further comprises exposing the composition to a polymerizing initiator in situ on the articular surface, whereby a cross-linked polymer is formed, smoothly coating the articular surface.

A method of assessing presence of cartilage degradation activity in a tissue sample is also provided, comprising providing a composition comprising a cross-linked polymer matrix and a detectable agent; providing a tissue sample; contacting the composition with a tissue sample; and, assessing release of a detectable agent from the composition. In some embodiments, the tissue sample may be derived from one or more biopsies of a skeletal joint. In other embodiments, a biopsy comprises obtaining articular cartilage or synovial fluid.

In another embodiment, a method of diagnosing arthritis in a subject is provided, comprising: providing a cross-linked polymer matrix comprising at least one monomeric unit of chondroitin sulfate, having entrapped therein a detectable agent; providing a tissue sample derived from skeletal joint biopsy of the subject; contacting the polymer matrix with the tissue sample; and assessing release of the detectable agent from the polymer matrix, wherein such release may indicate the presence of cartilage degrading activity associated with arthritis in the subject.

In yet another embodiment, a solid support comprising a surface substantially coated with a film is provided, wherein the film comprises a cross-linked polymer matrix, comprising at least one monomeric unit of chrondoitin sulfate. In some embodiments, a detectable agent is entrapped within the film.

A kit is provided in the instant disclosure, where the kit may be used for assessing presence of cartilage degradation activity in a tissue sample, and where the kit comprises a solid support according to this disclosure, a means for producing a solution sufficient for chondroitinase activity, and instructions for use. In some embodiment, means for producing a solution sufficient for chondrotinase activity comprises a container having therein a solution of Tris-HCl buffered to pH 8.0.

In another embodiment, a method for reconstructing cartilage in a subject in need thereof is provided, comprising: administering a composition comprising at least one monomeric unit of functionalized chondroitin sulfate to a site of desired cartilage formation in the subject. In some embodiments, the composition further comprises viable cartilage forming cells suspended therein. The method may further comprise photoirradiating the composition in situ, thereby forming a chrondroitin sulfate cross-linked matrix having the cells entrapped therein.

Further, a second method for reconstructing cartilage in a subject in need thereof is provided, comprising: providing a cross-linked polymer matrix comprising at least one unit of functionalized chondroitin sulfate; and implanting the polymer matrix into the subject at a site in need of reconstructing. The cross-linked polymer matrix may further comprise cells, such as chondrocytes or mesenchymal stem cells entrapped therein. The site of desired cartilage formation may be a skeletal joint, or an intervertebral disk, nose or ear.

In yet another embodiment, a method of sealing or filling a wound in a subject in need thereof is provided, comprising: administering a composition comprising functionalized chondroitin sulfate. The method may further comprise using a composition that further comprises biocompatible polymer or an compound comprising an amine moiety, thereby forming a cross-linked matrix that fills or seals the wound.

DETAILED DESCRIPTION OF THE INVENTION

1. Overview

Figure 1:
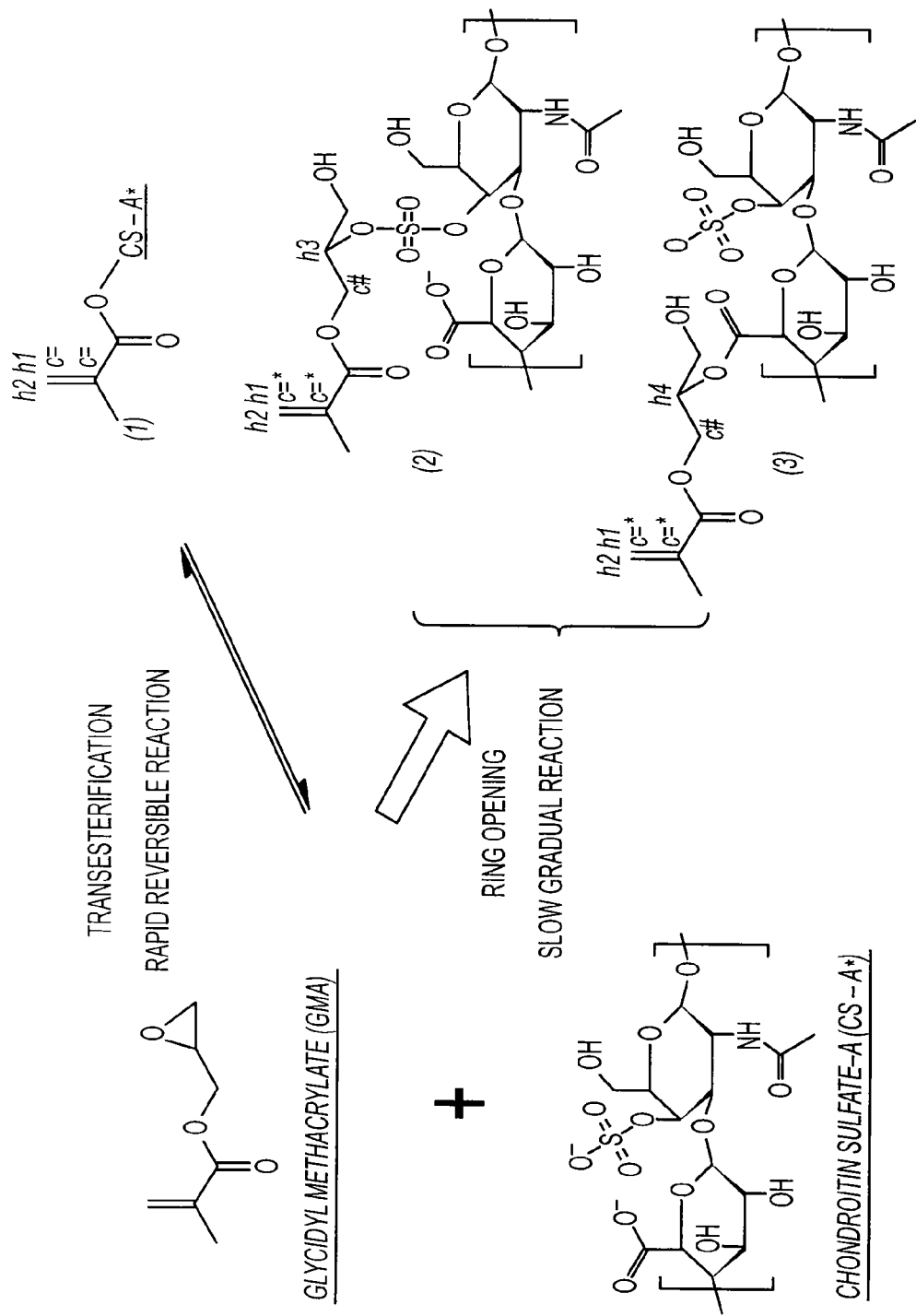
FIG. 1 is a schematic illustration depicting synthetic pathways of methacrylated chondroitin sulfate (CS-MA), with proton/carbon labels h* and c*.

This disclosure is directed, at least in part, to cross-linked polymers, matrices, and gels, and methods of making and using cross-linked matrices, polymers and gels. Such cross-linked polymers may comprise a functionalized saccharide.

For example, this disclosure provides for functionalized chondroitin sulfate. Functionalized chondroitin sulfate may form a cross-linked polymer matrix, which may be useful for, for example, cartilage reconstruction, for example, in a skeletal joint, and sealing or filling a wound. A cross-linked polymer matrix that includes a functionalized saccharide may also be useful for use in detecting the presence of cartilage degradation activity.

2. Definitions

For convenience, before further description of the present disclosure, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "articulation surface" refers to the surface of, and also to the disk of, cartilage between two bones in a joint. Reference herein to "articulating surface" refers to the well-known fact that, in a healthy joint, two cartilage-covered surfaces on two different bones will rub, slide, roll, or otherwise move while in contact with each other, as the joint is flexed or extended. This type of mobile interaction between two such surfaces is referred to as articulation, and the two cartilage-covered surfaces that contact and press against each other during such motion are said to "articulate". The disk of cartilage between two bones in a joint may be referred to as "articular cartilage".

The terms "active agent," and "biologically active agent" are used interchangeably herein to refer a chemical or biological compound that induces a desired pharmacological, physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, it is to be understood that applicants intend to include the active agent per se as well as pharmaceutically acceptable, pharmacologically active salts, esters, amides, prodrugs, metabolites, analogs, etc.

The terms "biocompatible polymer", "biocompatible cross-linked polymer matrix" and "biocompatibility" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively nontoxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1M NaOH at 37° C. until complete degradation is observed. The solution is then neutralized with 1M HCl. About 200 µL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers, polymer matrices, and formulations of the present invention may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, polymer matrices, gels, compositions and formulations, such as those described herein, that are intended to degrade during use. Biodegradable polymers and matrices typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to side chain or that connects a side chain to the polymer backbone. For example, a therapeutic agent, biologically active agent, or other chemical moiety attached as a side chain to the polymer backbone may be released by biodegradation. In certain embodiments, one or the other or both generally types of biodegradation may occur during use of a polymer. As used herein, the term "biodegradation" encompasses both general types of biodegradation.

The degradation rate of a biodegradable polymer often depends in part on a variety of factors, including the chemical identity of the linkage responsible for any degradation, the molecular weight, crystallinity, biostability, and degree of cross-linking of such polymer, the physical characteristics of the implant, shape and size, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments, the biodegradation rate of such polymer may be characterized by the presence of enzymes, for example a chondroitinase. In such circumstances, the biodegradation rate may depend on not only the chemical identity and physical characteristics of the polymer matrix, but also on the identity of any such enzyme.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between about 25 and 37° C. In other embodiments, the polymer degrades in a period of between about one hour and several weeks, depending on the desired application. In some embodiments, the polymer or polymer matrix may include a detectable agent that is released upon degradation.

The term "cartilage degradation activity" refers to an activity or the presence of a substance that may lead to the degradation of cartilage, for example, the activity or presence of degrading enzymes, or the presence of fibrillation, erosion or cracking on the cartilage.

The term "cartilage forming cells" include cells that form or promote formation of cartilage. Such cells include chondrocytes and mesechymal stem cells.

The term "cross-linked" herein refers to a composition containing intermolecular cross-links and optionally intramolecular cross-links, arising from the formation of covalent bonds. Covalent bonding between two cross-linkable components may be direct, in which case an atom in one component is directly bound to an atom in the other component, or it may be indirect, through a linking group. A cross-linked gel or polymer matrix may, in addition to covalent bonds, also include intermolecular and/or intramolecular noncovalent bonds such as hydrogen bonds and electrostatic (ionic) bonds. The term "cross-linkable" refers to a component or compound that is capable of undergoing reaction to form a cross-linked composition.

"Electromagnetic radiation" as used in this specification includes, but is not limited to, radiation having the wavelength of $10^{-20}$ to 10 meters. Particular embodiments of electromagnetic radiation of the present invention employ the electromagnetic radiation of: gamma-radiation ($10^{-20}$ to $10^{-13}$ m), x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

The term "functionalized" refers to a modification of an existing molecular segment to generate or introduce a new reactive functional group (e.g., acrylate group) that is capable of undergoing reaction with another functional group (e.g., a sulfhydryl group) to form a covalent bond. For example, carboxylic acid groups can be functionalized by reaction with an acyl halide, e.g., an acyl chloride, again using known procedures, to provide a new reactive functional group in the form of an anhydride.

The term "gel" refers to a state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two dimensional surface.) "Gelation time," also referred to herein as "gel time," refers to the time it takes for a composition to become non-flowable under modest stress. This is generally exhibited as reaching a physical state in which the elastic modulus G' equals or exceeds the viscous modulus G", i.e., when tan (delta) becomes 1 (as may be determined using conventional rheological techniques).

The term "hydrogel" is used to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-inking.

The term "instructional material" or "instructions" includes a publication, a recording, a diagram, or any other medium of expression which can be used to communicate the usefulness of a subject composition described herein for a method of treatment or a method of making or using a subject composition. The instructional material may, for example, be affixed to a container which contains the composition or be shipped together with a container which contains the composition or be contained in a kit with the composition. Alternatively, the instructional material may be shipped separately from the container with the intention that the instructional material and the composition be used cooperatively by the recipient.

The term "polymer" is used to refer to molecules composed of repeating monomer units, including homopolymers, block copolymers, random copolymers, and graft copolymers. "Polymers" also include linear polymers as well as branched polymers, with branched polymers including highly branched, dendritic, and star polymers.

A "polymerizing initiator" refers to any substance or stimulus, that can initiate polymerization of monomers or macromers by free radical generation. Exemplary polymerizing initiators include electromagnetic radiation, heat, and chemical compounds.

As used herein, the term "saccharide", refers to a mono-, di-, tri-, or higher order saccharide or oligosaccharide. Representative monosaccharides include glucose, mannose, galactose, glucosamine, mannosamine, galactosamine, fructose, glyceraldehyde, erythrose, threose, ribose, arabinose, xylose, lyxose, allose, altrose, gluose, idose, talose, psicose, sorbose, and tagatose. Exemplary disaccharides include maltose, lactose, sucrose, cellobiose, trehalose, isomaltose, gentiobiose, melibiose, laminaribiose, chitobiose, xylobiose, mannobiose, sophorose, and the like. Certain tri- and higher oligosaccharides include raffinose, maltotriose, isomaltotriose, maltotetraose, maltopentaose, mannotriose, manninotriose, etc. Exemplary polysaccharides include starch, sodium starch glycolate, alginic acid, cellulose, carboxymethylcellulose, hydroxyethylcellulose, hydropropylcellulose, hydroxypropylmethylcellulose, ethylcellulose, carageenan, chitosan, chondroitin sulfate, heparin, hyaluronic acid, and pectinic acid.

As used herein, a "saccharide unit" refers to a saccharide molecule having at least one pyranose or furanose ring. In some embodiments, at least one hydrogen atom may be removed from a hydroxyl group of a saccharide unit, as when the hydroxyl group has been esterified.

The term "detectable agent" includes those agents that may be used for diagnostic purposes. Examples of such diagnostic agents include imaging agents that are capable of generating a detectable image. Such imaging agents shall include dyes, radionuclides and compounds containing them (e.g., tritium, iodine-125, iodine-131, iodine-123, iodine-124, astatine-210, carbon-11, carbon-14, nitrogen-13, fluorine-18, Tc-99m, Re-186, Ga-68, Re-188, Y-90, Sm-153, Bi-212, Cu-67, Cu-64, and Cu-62), unpaired spin atoms and free radicals (e.g., Fe, lanthanides, and Gd), contrast agents (e.g., chelated (DTPA) manganese), and fluorescent or chemiluminescent agents.

The term "treating" or "treatment" is an art-recognized term which includes curing as well as ameliorating at least one symptom of any condition or disease. Treating includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing regression of the disease, disorder and/or condition. Further, treating the disease or condition includes ameliorating at least one symptom of the particular disease or condition, even if the underlying pathophysiology is not affected.

Viscosity is understood herein as it is recognized in the art to be the internal friction of a fluid or the resistance to flow exhibited by a fluid material when subjected to deformation. The degree of viscosity of the polymer can be adjusted by the molecular weight of the polymer, as well as by mixing different isomers of the polymer backbone; other methods for altering the physical characteristics of a specific polymer will be evident to practitioners of ordinary skill with no more than routine experimentation. The molecular weight of the polymer used in the composition of the invention can vary widely, depending on whether a rigid solid state (usually higher molecular weights) desirable, or whether a fluid state (usually lower molecular weights) is desired.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci., 66:1-19 (1977).

A "patient," "subject," or "host" to be treated by the subject method may mean either a human or non-human animal, such as primates, mammals, and vertebrates.

The terms "prophylactic" or "therapeutic" treatment are art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The term "synovial fluid" refers to the liquid produced by the synovial membranes of a joint. Synovial fluid may act as a lubricant.

The terms "incorporated", "encapsulated", and "entrapped" are art-recognized when used in reference to a therapeutic agent, dye, or other material and a polymeric composition, such as a composition of the present invention. In certain embodiments, these terms include incorporating, formulating or otherwise including such agent into a composition which allows for sustained release of such agent in the desired application. The terms may contemplate any manner by which a therapeutic agent or other material is incorporated into a polymer matrix, including for example: attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the sustained release of any encapsulated therapeutic agent or other material determines whether the form of encapsulation is sufficiently acceptable for any particular use.

A "wound closing device" includes devices and materials that may close or assist in closing a wound, such as for example, sutures, staples, sealants, and glues or adhesives.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., C1-C30 for straight chain, C3-C30 for branched chain), and alternatively, about 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls may be further substituted with alkyls, alkenyls, alkoxys, alkylthios, aminoalkyls, carbonyl-substituted alkyls, —CF3, —CN, and the like.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

A "methacrylate" refers to a vinylic carboxylate, for example, a methacrylic acid in which the acidic hydrogen has been replaced. Representative methacrylic acids include acrylic, methacrylic, α-chloroacrylic, α-cyano acrylic, α-ethylacrylic, maleic, fumaric, itaconic, and half esters of the latter dicarboxylic acids.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "carbocycle" is art recognized and includes an aromatic or non-aromatic ring in which each atom of the ring is carbon. The following art-recognized terms have the following meanings: "nitro" means —NO2; the term "halogen" designates —F, —Cl, —Br or —I; the term "sulfhydryl" means —SH; the term "hydroxyl" means —OH; and the term "sulfonyl" means —SO2-.

The terms "amine" and "amino" are art-recognized and include both unsubstituted and substituted amines, e.g., a moiety that may be represented by the general formulas:

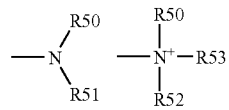

wherein R50, R51 and R52 each independently represent a hydrogen, an alkyl, an alkenyl, —(CH2)m-R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH2)m-R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

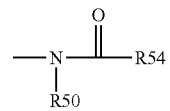

wherein R50 is as defined above, and R54 represents a hydrogen, an alkyl, an alkenyl or —(CH2)m-R61, where m and R61 are as defined above.

The term "anido" is art-recognized as an amino-substituted carbonyl and includes a moiety that may be represented by the general formula:

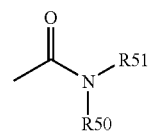

wherein R50 and R51 are as defined above. Certain embodiments of the amide in the present invention will not include imides which may be unstable.

The term "alkylthio" is art-recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH2)m-R61, wherein m and R61 are defined above. Representative alkylthio groups include methylthio, ethyl thio, and the like.

The term "carbonyl" is art-recognized and includes such moieties as may be represented by the general formulas:

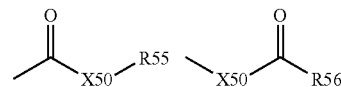

wherein X50 is a bond or represents an oxygen or a sulfur, and R55 represents a hydrogen, an alkyl an alkenyl, —(CH2)m-R61or a pharmaceutically acceptable salt, R56 represents a hydrogen, an alkyl, an alkenyl or —(CH2)m-R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH2)m-R61, where m and R61 are described above.

The term "sulfonate" is art-recognized and includes a moiety that may be represented by the general formula:

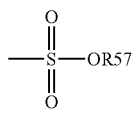

in which R57 is an electron pair, hydrogen, alkyl, cycloalkyl, or aryl.

The term "sulfate" is art-recognized and includes a moiety that may be represented by the general formula:

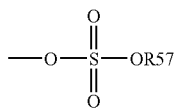

in which R57 is as defined above.

The term "sulfonamido" is art-recognized and includes a moiety that may be represented by the general formula:

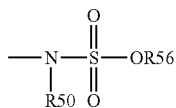

in which R50 and R56 are as defined above.

The term "sulfamoyl" is art-recognized and includes a moiety that may be represented by the general formula:

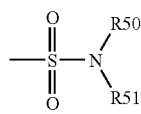

in which R50 and R51 are as defined above.

The term "sulfonyl" is art-recognized and includes a moiety that may be represented by the general formula:

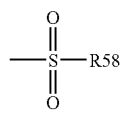

in which R58 is one of the following: hydrogen, alkyl alkenyl, alkynyl, cycloalkyl, heterocyclyl, aryl or heteroaryl.

The term "sulfoxido" is art-recognized and includes a moiety that may be represented by the general formula:

in which R58 is defined above.

The term "phosphoramidite" is art-recognized and includes moieties represented by the general formulas:

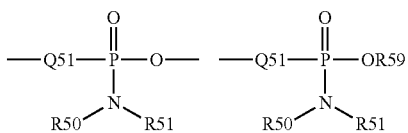

wherein Q51, R50, R51 and R59 are as defined above.

The term "phosphonamidite" is art-recognized and includes moieties represented by the general formulas:

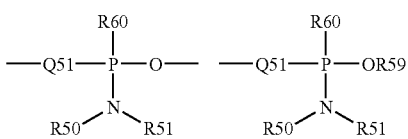

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

The term "selenoalkyl" is art-recognized and includes an alkyl group having a substituted seleno group attached thereto. Exemplary "selenoethers" which may be substituted on the alkyl are selected from one of —Se-alkyl, —Se-alkenyl, —Se-alkynyl, and —Se—(CH2)m-R61. m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain monomeric subunits of the present invention may exist in particular geometric or stereoisomeric forms. In addition, polymers and other compositions of the present invention may also be optically active. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87, inside cover. The term "hydrocarbon" is art recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., Protective Groups in Organic Synthesis 2nd ed., Wiley, New York, (1991).

The phrase "hydroxyl-protecting group" is art-recognized and includes those groups intended to protect a hydroxyl group against undesirable reactions during synthetic procedures and includes, for example, benzyl or other suitable esters or ethers groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, March, Advanced Organic Chemistry 251-59, McGraw Hill Book Company, New York, (1977). The Hammett constant values are generally negative for electron donating groups ($\sigma(P)=-0.66$ for NH2) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

In some embodiments, this disclosure directed to a composition comprising at least one monomeric unit of a saccharide, such as chondroitin sulfate, functionalized by at least one polymerizable moiety. Chondroitin sulfate is a natural component of cartilage and may be a useful scaffold material for its regeneration. Chrondroitin sulfate includes members of 10-60 kDa glycosaminoglycans. The repeat units, or monomeric units, of chrondroitin sulfate consist of a disaccharide, beta(1-4)-linked D-glucuronyl beta(1-3)N-acetyl-D-galactosamine sulfate.

A polymerizable moiety includes any moiety that is capable of polymerizing upon exposure to a polymerizing initiator. A polymerizable moiety may include alkenyl moieties such as acrylates, methacrylates, dimethacrylates, oligoacrylates, oligomethoacrylates, ethacrylates, itaconates, acrylamides. Further polymerizable moieties include aldehydes. Other polymerizable moieties may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene, and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid, and styrene carboxylic acid. Suitable polyethylenically unsaturated monomers include butadiene, isoprene, allylmethacrylate, diacrylates of alkyl diols such as butanediol diacrylate and hexanediol diacrylate, divinyl benzene and the like.

In some embodiments, a monomeric unit of chondroitin sulfate may be functionalized through one or more thio, carboxylic acid or alcohol moieties located on a monomer of chrondroitin sulfate.

Functionalized monomeric chrondroitin sulfate may be represented by Formula I, II or III:

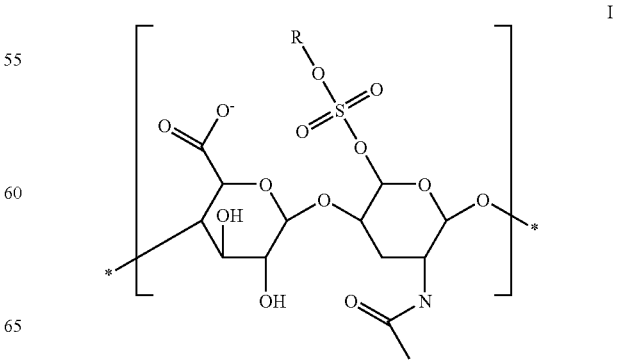

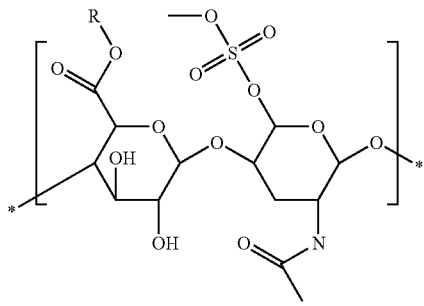

II

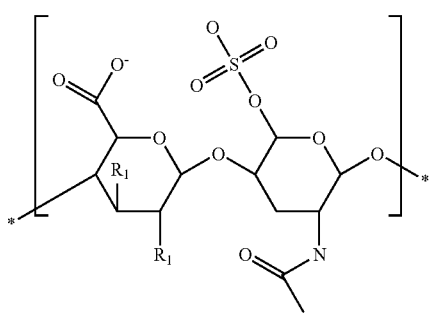

III wherein R is alkenyl, and $R_1$ is independently selected from aldehyde or alcohol, wherein at least one $R_1$ is an aldehyde.

In some embodiments, R is

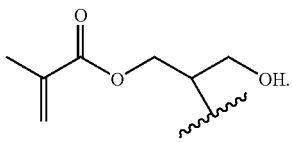 [SMILES: *C(CO)COC(=O)C(=C)C]

For example, a functionalized monomer unit of chrondroitin sulfate may be represented by:

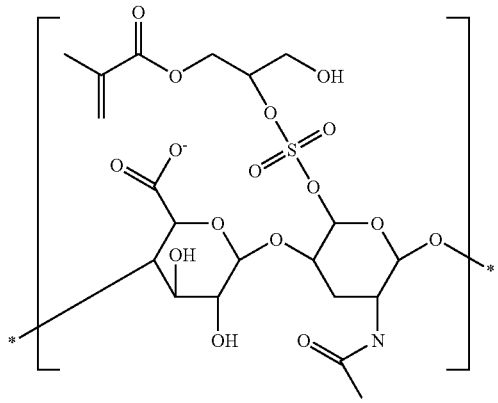

I

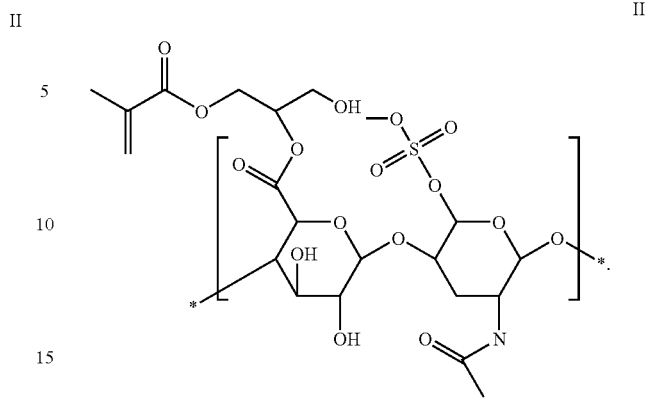

II

Chondroitin sulfate (CS) is a natural component of cartilage and therefore may be a useful scaffold material for cartilage regeneration. A monomeric unit of CS may be represented by:

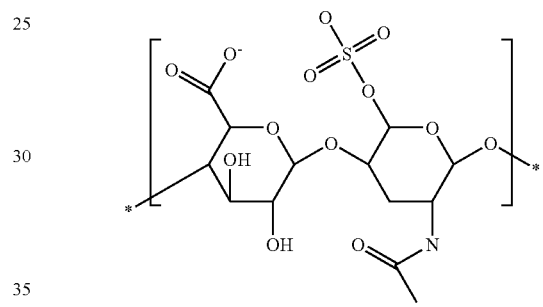

Representative embodiments of the invention include a method of producing a functionalized saccharide moiety is provided, where the method includes providing a solution comprising at least one saccharide moiety, and an alkylene moiety; and stirring said solution for example, at least 10 days, at least 11 days, or at least 15 days. Alternatively, the solution may be stirred or maintained for about 10 to about 15 days, or about 14 to about 15 days. The solution may include a polar solvent, for example an aqueous solvent.

Figure 2:
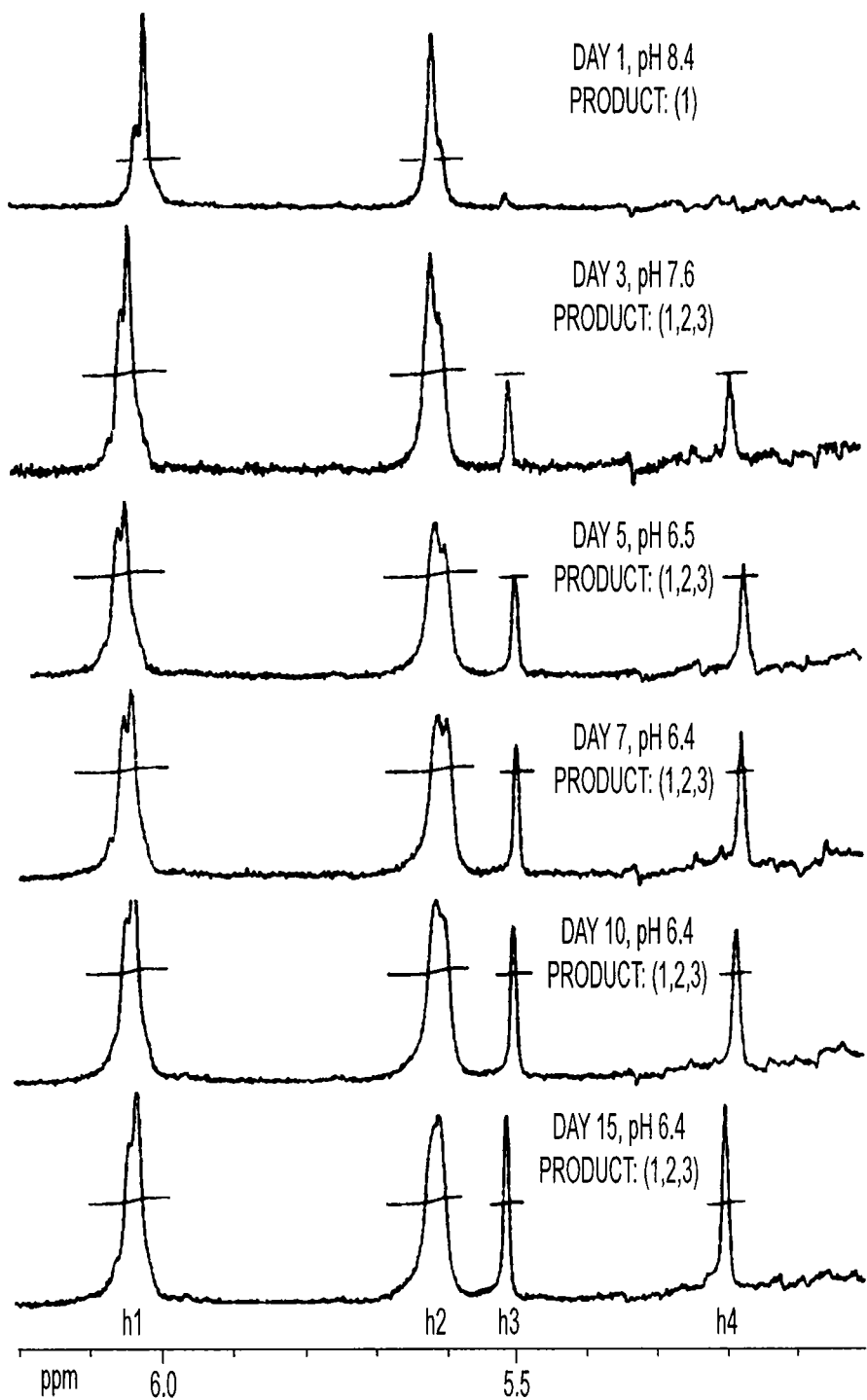
FIG. 2 is a line graph depicting $^1$H NMR spectra that indicate the free methacrylate-conjugation of chondrotian sulfate. Curves from the top to bottom represent, respectively, days 1, 3, 5, 7, 10 and 15.
Figure 3:
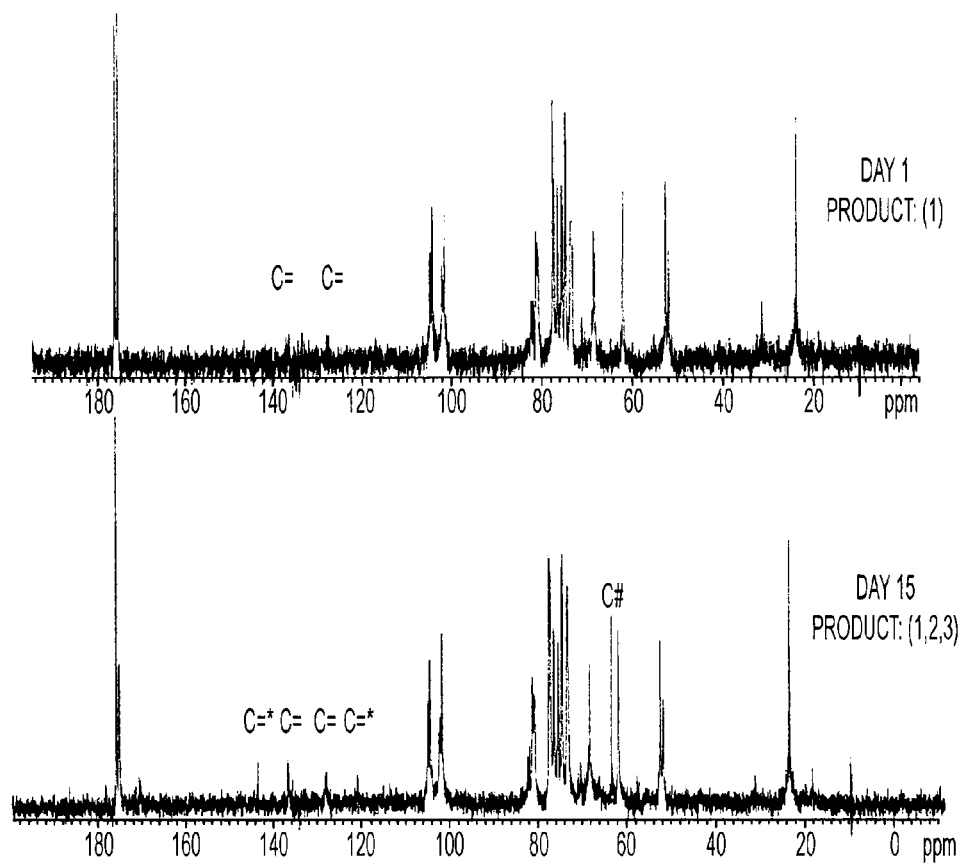
FIG. 3 is a line graph showing the $^{13}$C NMR spectra indicating the free methacrylate-conjugation of chondroitin sulfate. Day 1 is depicted in the upper panel, and Day 15 depicted in lower panel.

An exemplary reaction scheme is provided in FIG. 1. The NMR spectra of GMA-CS are provided in FIGS. 2 and 3. The assignments of the relevant NMR peaks are demonstrated by the corresponding hydrogen/carbon-labels in FIG. 1. The two 1H-NMR peaks (marked "h1" and "h2") represent the two vinyl protons at $\delta_{vinyl-H}$ 6.03 ppm and 5.61 ppm respectively. These peaks are utilized to determine the presence of methacrylate groups on chondroitin sulfate (CS). After one day of methacrylation, the introduction of "h1" and "h2" in the H-NMR indicated the initial methacrylation of CS. Methacrylation is also confirmed by $^{13}$C-NMR (FIG. 3) with vinyl-carbon peaks (labeled with "C=") present at $\delta c$=136 ppm and 128 ppm.

The lack of spectrometric evidences for glyceryl spacers and the considerable stability of the glycidol leaving group, may confirm that the transesterification reaction dominated via reversible cleaving of the electronegative glycidol in the first day of the reaction. From Day 3-15, the glyceryl methine protons at 5.51 ppm (labelled "h3") and 5.20 ppm ("h4") begin to emerge on H-NMR, with an intensity that increases with time. On the C-NMR spectrum at Day 15, the vinyl-carbon peaks are split into four; the original two peaks (Peak "C=") were enhanced, and two newly arisen peaks (marked with "C") are present at 121 ppm and 143 ppm respectively. These addition peaks also show the presence of the glyceryl spacer. Moreover, the further evidence of ring-opening by 13C-NMR is the emergence of the peak at 63 ppm (marked with "C#") that represents the skeleton carbon on the glyceryl spacer. The glyceryl moieties originate from the ring-opening reaction on GMA's glycidyl residue. The two ring-opening products are indicated in Scheme 1 as the compounds (2) and (3).

Figure 12A:
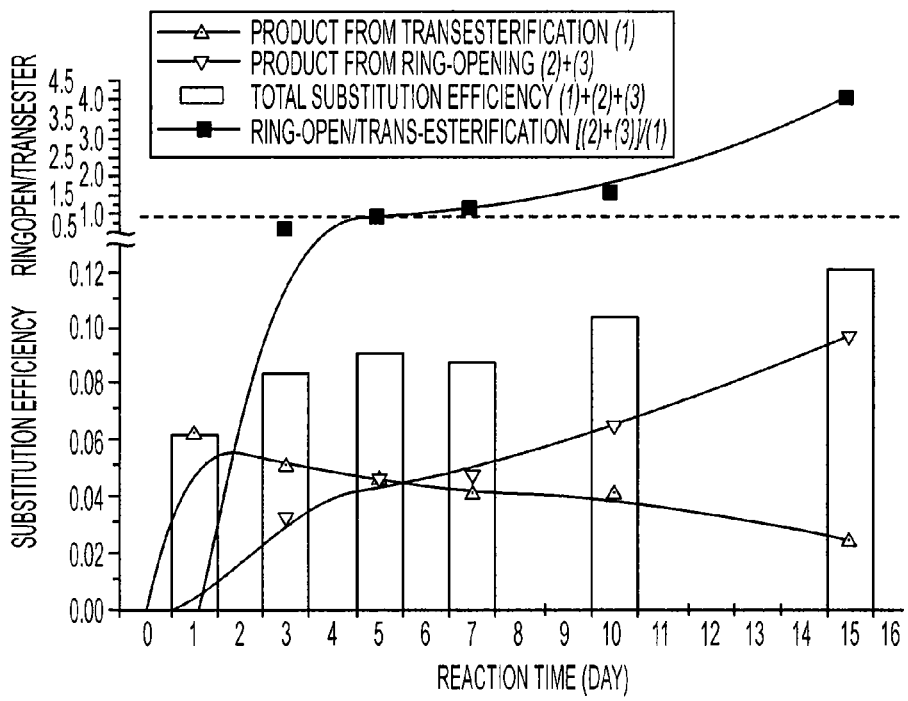
FIG. 12 is a line drawing depicting kinetic curves for substitution efficiency of the free methacrylate-conjugation: (A) total substitution efficiency and contributions by ring opening and transesterification; (B) individual contributions by the two ring opening products (2 and 3).
Figure 12B:
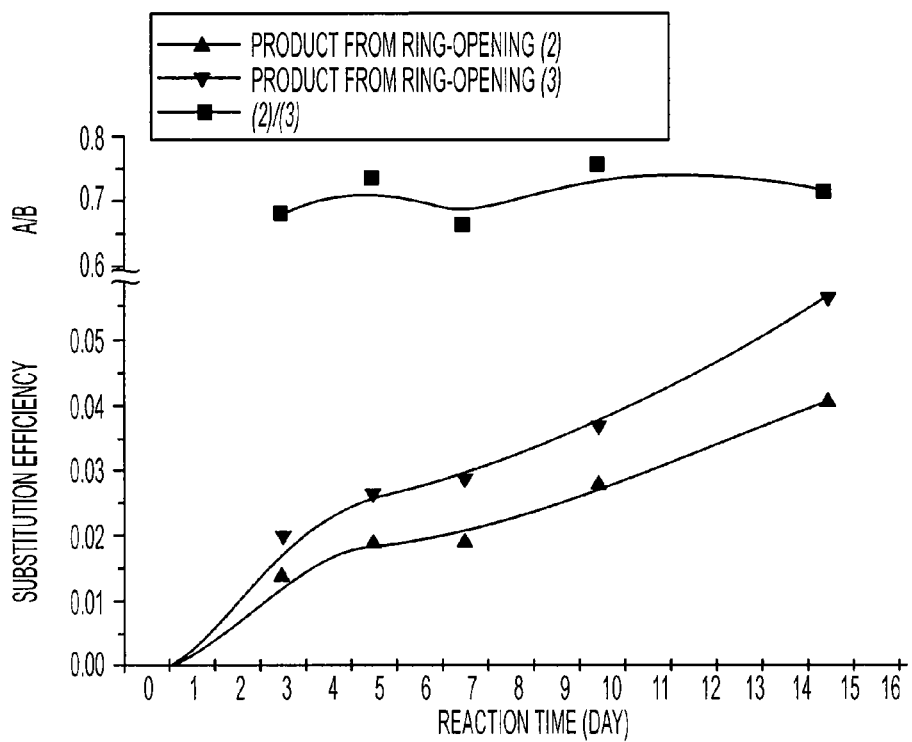

A quantitative analysis may be based an $^1$H-NMR data. The integral of vinyl-proton peaks "h1" and "h2", [h1]+[h2], are contributed by both transesterification product (1) and ring-opening products (2), (3). The ring-opening products (2) and (3) have their characteristic glyceryl methine peaks respectively at "h3" and "h4". Since the peaks "h1~4" are all representing single protons, the gross substitution efficiency may be calculated as ([h1]+[h2])/2, in which the contribution of ring-opening is ([h3]+[h4]), as shown in FIG. 12. The transesterification may be a kinetically rapid and thermodynamically reversible procedure. Within 1 day or so, a reaction balance is reached, with a yield of about 50% gross substitution efficiency of the transesterification product. The ring-opening procedure may be kinetically slower, and therefore not substantially detectable after only 1 day. However, the ring-opening procedure is based on a thermodynamically irreversible mechanism. The reaction may proceed substantially linearly and may be independent of other procedures. At Day 5, contributions for gross methacrylation by the two reaction mechanisms becomes about equal. By day 15, the ring-opening mechanism may contribute to more than 80% of the substitution efficiency while products of the transesterification may be reduced to less than about 20%.

Figure 13:
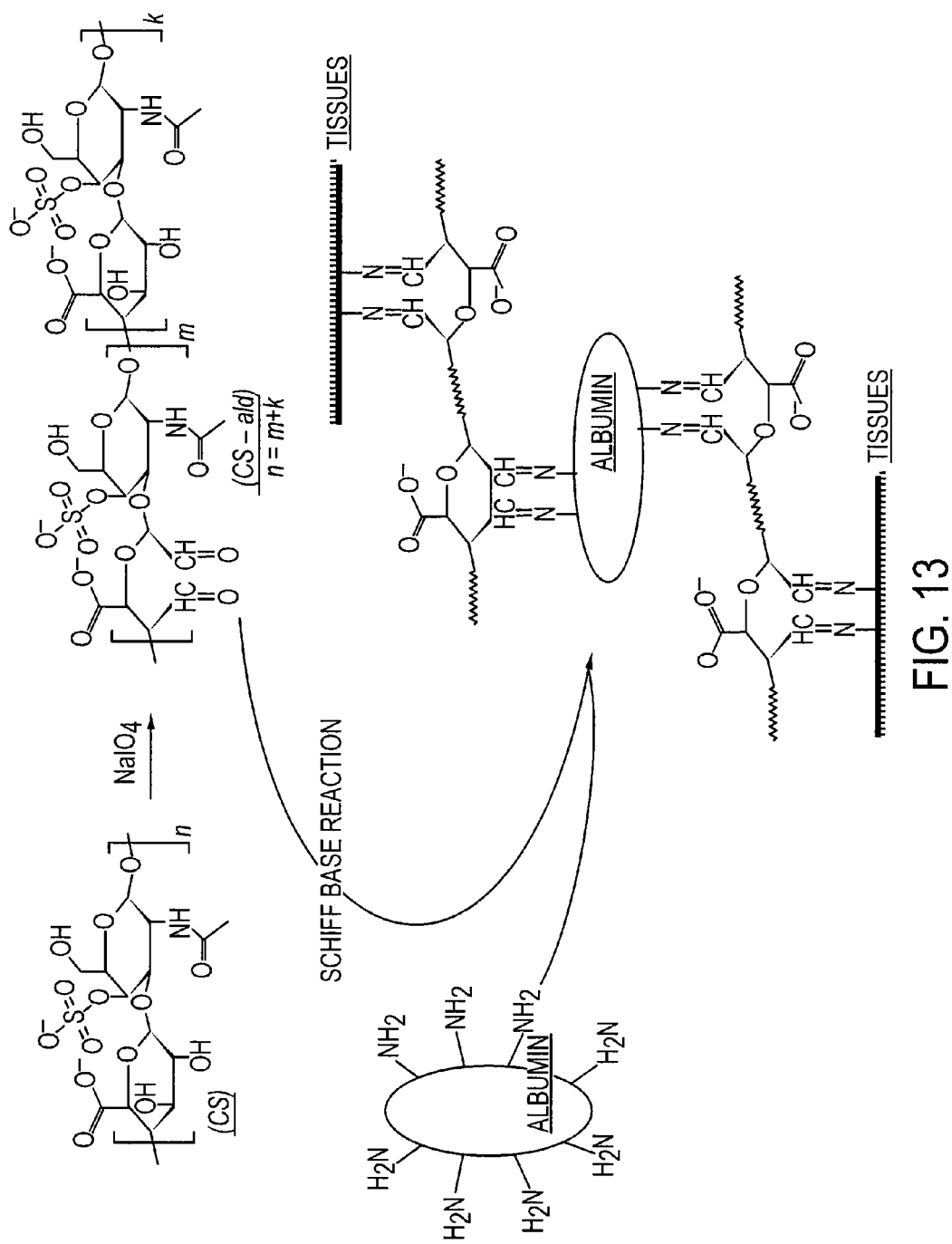
FIG. 13 is a schematic illustration depicting one synthetic pathway of chrondroitin sulfate functionalized with an aldehyde, and the formation of a cross-linked polymer matrix using albumin.

Another reaction scheme for creating functionalized chondroitin sulfate is shown in FIG. 13. An exemplary functionalized monomeric unit of chonroitin sulfate may be represented by:

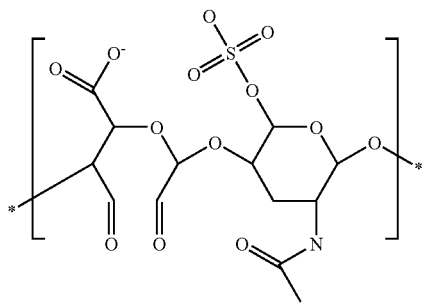

Numerous chemical options are available for modifying polymers that may then undergo a radical polymerization For example, methacrylic anhydride, methacryloyl chloride, and glycidyl methacrylate may be used to add methacrylate groups to one or more monomers of a polymer chain. Glycidyl methacrylate may be used, for example, for efficiency of reaction. Further, the modification reagents may be chosen to optimize a lack of cytotoxic byproducts.

In some embodiments, the number of polymerizing moieties per polymeric unit may be at least one moiety per about 10 monomeric units, or at least about 2 moieties per about 10 monomeric units. Alternatively, number of polymerizing moieties per polymeric unit may be at least one moiety per about 12 monomeric units, or per about 14 monomeric units. For example, there may be at least about one methacrylate group per ten chondroitin sulfate disaccharide units. In an embodiment, chondroitin sulfate may be functionalized with about 12% methacrylate groups.

This disclosure also provides for a composition comprising a cross-linked polymer matrix, wherein said cross-linked polymer matrix comprises at least one monomeric unit of functionalized chrondoitin sulfate. In some embodiments, said cross-linked polymer matrix further comprises least one monomeric unit of a biocompatible polymer. In other embodiments, a cross-linked polymer matrix further comprises a compound comprising one or more amine groups, such as for example, a protein.

Suitable polymers include biocompatible monomers with recurring units found in poly(phosphoesters), poly(lactides), poly(glycolides), poly(caprolactones), poly(anhydrides), poly(amides), poly(urethanes), poly(esteramides), poly(orthoesters), poly(dioxanones), poly(acetals), poly(ketals), poly(carbonates), poly(orthocarbonates), poly(phosphazenes), poly(hydroxybutyrates), poly(hydroxy-valerates), poly(alkylene oxalates), poly(alkylene succinates), poly(malic acids), poly(amino acids), poly(vinylpyrrolidone), poly(ethylene glycol), poly(hydroxycellulose), chitin, chitosan, and copolymers, terpolymers, or combinations or mixtures of the above materials.

Other suitable synthetic polymers include polymers containing amine groups, such as chemically synthesized polypeptides. Such polypeptides may include polynucleophilic polypeptides that have been synthesized to incorporate amino acids containing primary amino groups for example, lysine and/or amino acids containing thiol groups (such as cysteine). Further suitable synthetic polymers include poly(amino)acids.

Other compounds that may include amine groups include proteins such as albumin. Albumin may be of mammalian origin, but other sources of albumin also may be employed. It is believed that most albumins are readily cross-linked according to the methods of the invention. Bovine serum albumin (BSA) may also be used. Alternatively, albumin may be recombinant albumin, isolated from cells expressing a recombinant albumin gene, using methods known in the art. Major fragments of albumin, comprising at least 100 residues of an albumin sequence, whether produced by partial proteolysis or by recombinant means, may also be used instead of intact albumin. Alternatively, useful fragments may contain at least 50 residues, and more preferably at least 75 residues of an albumin sequence. Finally, mixtures of different forms of albumin (e.g., human, bovine, recombinant, fragmented), and plasma fractions rich in albumin may also be employed. Albumin may be purified directly from tissues or cells, using methods well known in the art.

The polymer matrix of the invention can also comprise additional biocompatible monomeric units so long as they do not interfere the desirable characteristics of the invention. Such additional monomeric units may offer even greater flexibility in designing the precise profile desired for targeted drug delivery, or tissue engineering, or the precise rate of biodegradability or biocompatibility desired for other applications.

In some embodiments, the cross-linked polymer matrix may comprise functionalized chrondoitin sulfate, with at least about 75%, at least about 50%, at least about 25%, or at least about 10% of said biocompatible polymer or a compound comprising an amine group, by weight. Alternatively, the cross-linked polymer matrix may comprise less than 25% said biocompatible polymer a compound comprising an amine group by weight.

In another embodiment, a method of producing a composition comprising a cross-linked polymer matrix is provided. A method of producing a composition comprising a cross-linked polymer matrix may comprise providing a polymer comprising at least one monomeric unit of functionalized chondroitin sulfate and exposing said polymer to at least one polymerizing initiator, whereby producing said cross-linked matrix.

Alternatively, a cross-linked polymer may be produced by providing a polymer comprising at least one monomeric unit of aldehyde functionalized chondroitin and providing a protein, such as, for example, a poly(amino)acid or albumin, such that the aldehyde functionalized chondroitin becomes cross-linked with, for example, the albumin. The reaction mechanism of such cross-linking may be a Schiff base reaction, as is known in the art.

A polymerization reaction of the present invention can be conducted by conventional methods such as mass polymerization, solution (or homogeneous) polymerization, suspension polymerization, emulsion polymerization, radiation polymerization (using γ-ray, electron beam or the like), or the like.

Polymerizing initiators include electromechanical radiation. Initiation of polymerization may be accomplished by irradiation with light at a wavelength of between about 200 to about 700 nm, or above about 320 nm or higher, or even between about 514 nm and about 365 nm. In some embodiments, the light intensity is about 10 m W/cm3.

Examples of other initiators are organic solvent-soluble initiators such as benzoyl peroxide, azobisisobutyronitrile (AIBN), di-tertiary butyl peroxide and the like, water soluble initiators such as ammonium persulfate (APS), potassium persulfate, sodium persulfate, sodium thiosulfate and the like, redox-type initiators which are combinations of such initiator and tetramethylethylene, $Fe^{2+}$ salt, sodium hydrogen sulfite or like reducing agent, etc.

Useful photoinitiators are those which can be used to initiate by free radical generation polymerization of monomers with minimal cytotoxicity. In some embodiments, the initiators may work in a short time frame, for example, minutes or seconds. Exemplary dyes for UV or visible light initiation include ethyl eosin 2,2-dimethoxy-2-phenyl acetophenone, 2-methoxy-2-phenylacetophenone, other acetophenone derivatives, and camphorquinone. In all cases, crosslinking and polymerization are initiated among macromers by a light-activated free-radical polymerization initiator such as 2,2-dimethoxy-2-phenylacetophenone or a combination of ethyl eosin ($10^{-4}$ to $10^{-2}$ M) and triethanol amine (0.001 to 0.1 M), for example.

Other photooxidizable and photoreducible dyes that may be used to initiate polymerization include acridine dyes, for example, acriblarine; thiazine dyes, for example, thionine; xanthine dyes, for example, rose bengal; and phenazine dyes, for example, methylene blue. These may be used with cocatalysts such as amines, for example, triethanolamine; sulphur compounds, for example, $RSO_2$ $R_1$, heterocycles, for example, imidazole; enolates; organometallics; and other compounds, such as N-phenyl glycine. Other initiators include camphorquinones and acetophenone derivatives.

Thermal polymerization initiator systems may also be used. Such systems that are unstable at 37° C. and would initiate free radical polymerization at physiological temperatures include, for example, potassium persulfate, with or without tetramethyl ethylenediamine; benzoylperoxide, with or without triethanolamine; and ammonium persulfate with sodium bisulfite.

Cross-linked polymer matrices of the present invention may include hydrogels. The water content of a hydrogel may provide information on the pore structure. Further, the water content may be a factor that influences, for example, the survival of encapsulated cells within the hydrogel. The amount of water that a hydrogel is able to absorb may be related to the cross-linking density and/or pore size. For example, the percentage of methacrylate groups on a functionalized chondroitin sulfate macromer may dictate the amount of water absorbable.

Figure 4:
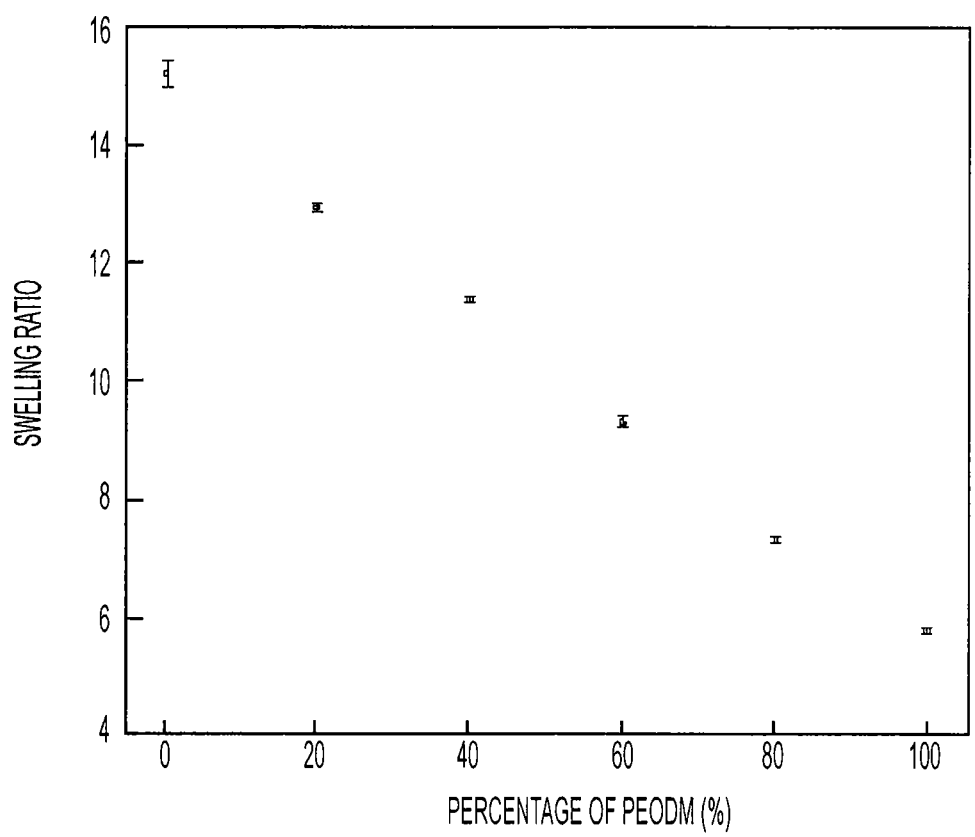
FIG. 4 is a line graph depicting the swelling ratio of cogels of CS-MA, varied as the function of the percentage of PEODM.

For example, poly(ethylene oxide)-diacrylate (PEODA) may be used in a polymer system for cartilage tissue engineering, and cross-linked polymer matrices may include cogels of CS-MA (chondroitin sulfate-methacrylate) and PEODA. The CS-MA hydrogels may absorb more water than the PEODA hydrogels, thus, increasing the percentage of CS-MA in the cogels increases the water content, as shown in FIG. 4.

The mechanical properties of a cross-linked polymer matrix, such as a hydrogel scaffold may also be related to the hydrogel pore structure. For applications in tissue engineering, scaffolds with different mechanical properties may be desirable depending on the desired clinical application. For example, scaffolds for cartilage tissue engineering in the articular joint must survive higher mechanical stresses than a cartilage tissue engineering system implanted subcutaneously for plastic surgery applications. Thus, hydrogels with mechanical properties that are easily manipulated may be desired.

Figure 5A:
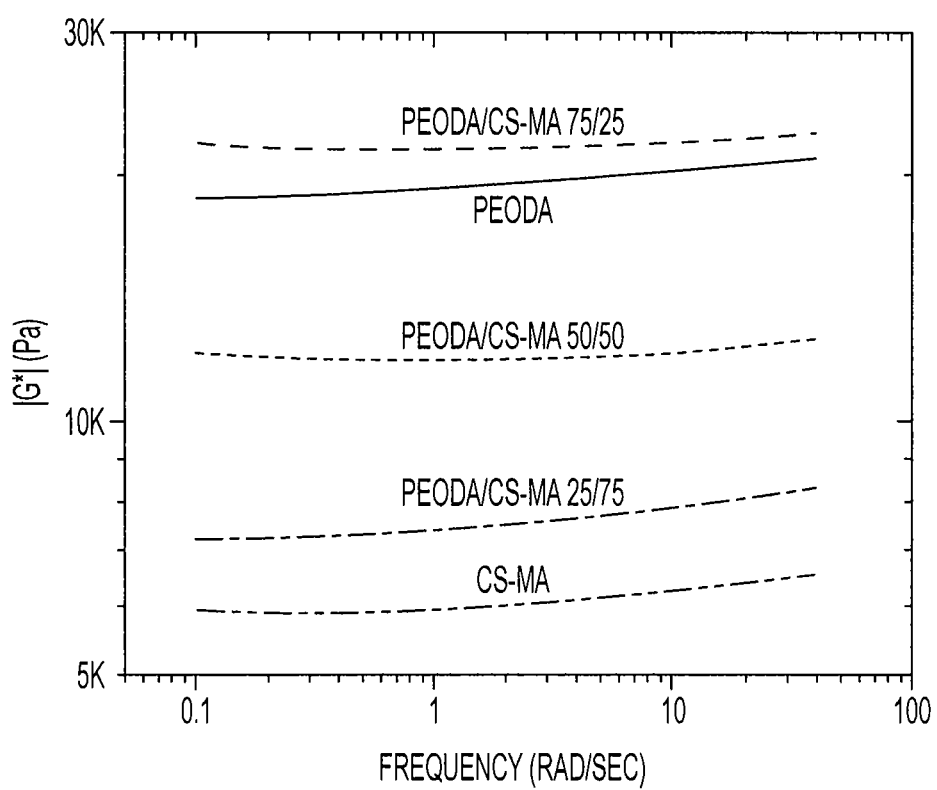
FIG. 5A is a line graph depicting the frequency of cogels of CS-MA and PEODA as a function of the dynamic shear modulus |G*|.
Figure 5B:
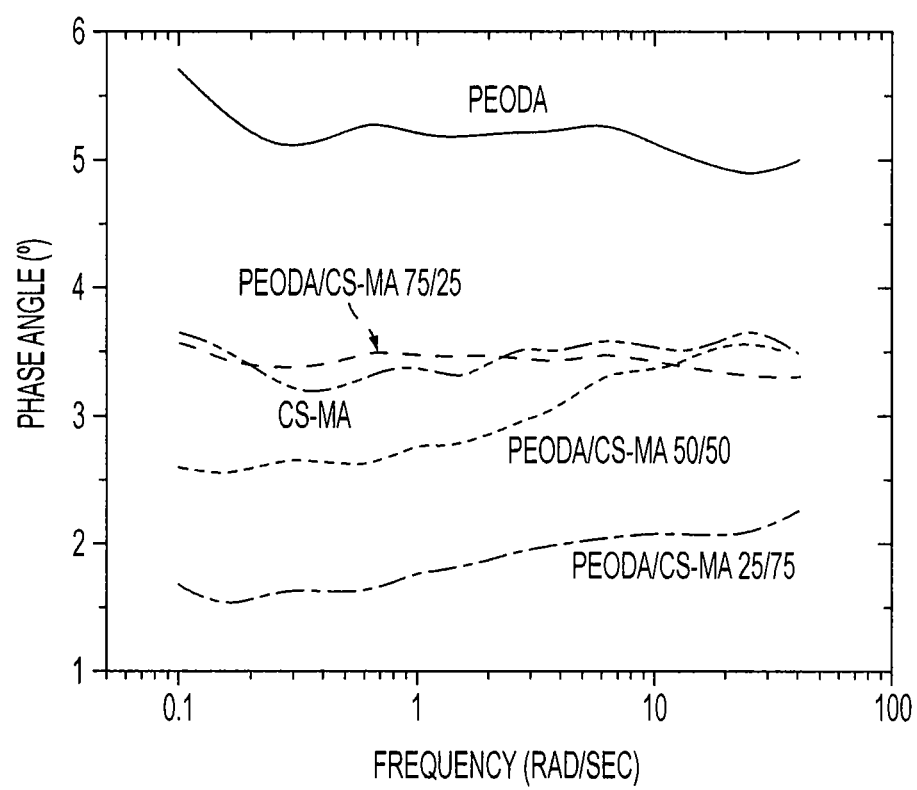
FIG. 5B is a line graph depicting the frequency of cogels of CS-MA and PEODA as a function of the phase angle δ.

The dynamic frequency-sweep experiments disclosed herein show that hydrogels with various PEODA/CS-MA ratios were elasticity dominant and not sensitive to the shear frequency (FIG. 5a). The norm of the dynamic shear modulus |G*| increases with the shear frequency; however, such increase may be insignificant compared with the average value of |G*|. The phase angle δ is narrowly ranged between about 1° and about 6° for all frequencies and all weight ratios. This may indicate that the rheological properties of PEODA and CS-MA are similar and the copolymerization does not alter these properties significantly. Cogels with higher portion of PEODA (100% and 75%) have a higher mechanical strength (indicated by |G*|) while the cogels with 50%, 25% and 0% PEODA exhibited a decrease of |G*| with the PEODA concentration (FIG. 5b). The 100% and 75% samples had a |G*| value 3-4 times that of the CS-MA gel. This is consistent with the swelling experiments that demonstrated that the PEODA gels are more highly cross-linked than the CS-MA gel.

Figure 6:
FIG. 6 is an image depicting the scanning electron micrograph image of the surface of CS-MA blocks (1200×), where the bar=2 µm.
Figure 7:
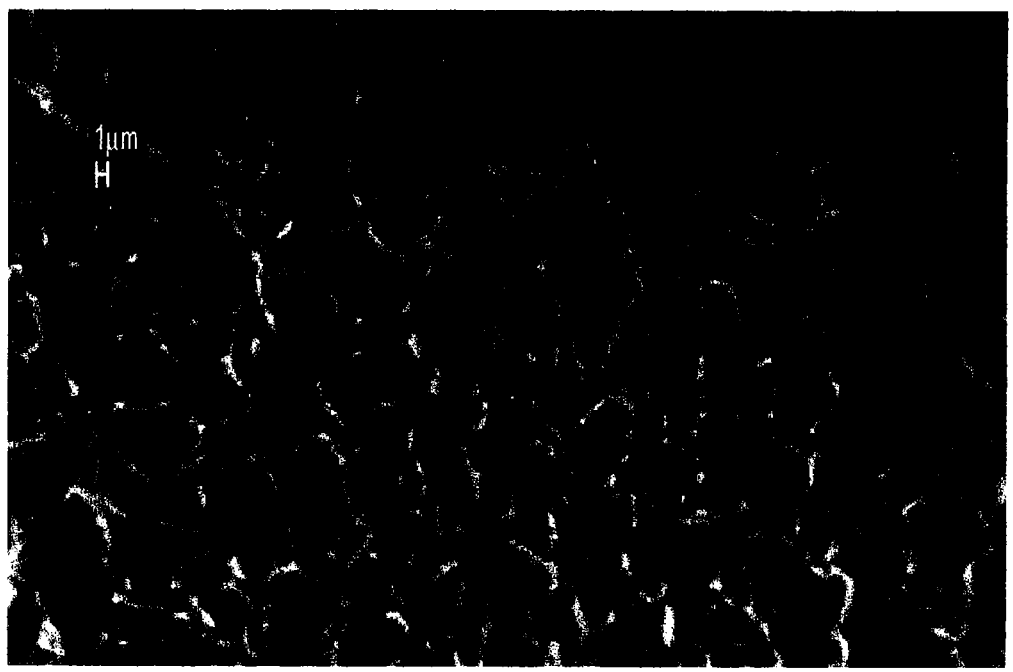
FIG. 7 is an image depicting the scanning electron micrograph image of the surface of CS-MA surface of PEODA blocks (2400×), bar=1 µm.
Figure 8A:
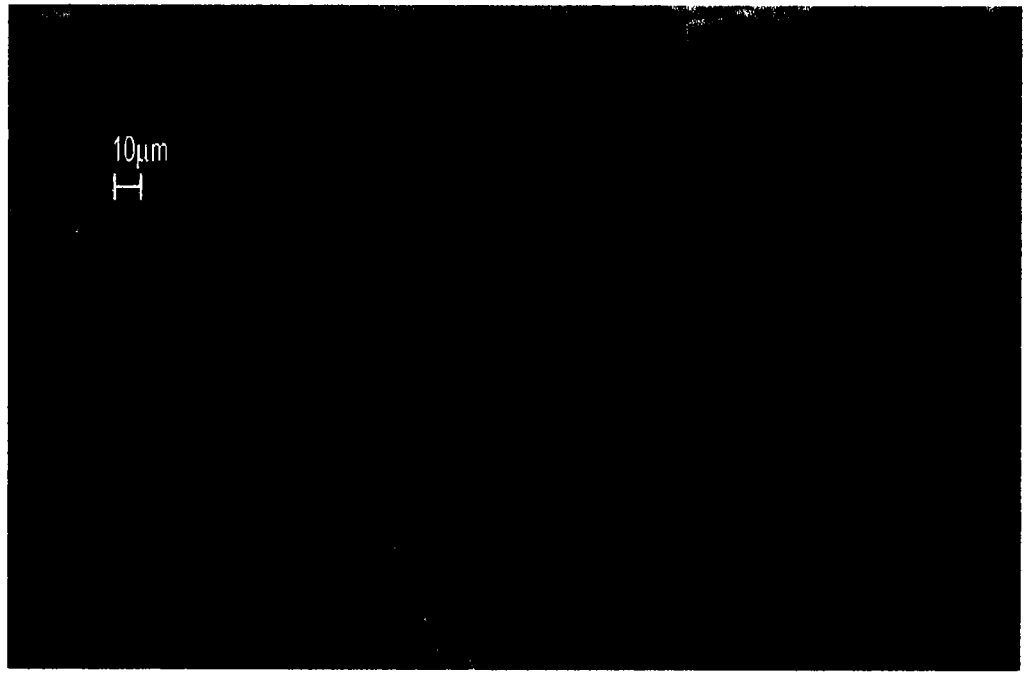
FIG. 8 is an image depicting the scanning electron micrograph of the surface of CS-MA where (A) the cut edge of CS-MA blocks (640×), bar=10 µm; (B) the cut edge of PEODA blocks (6400×), bar=1 µm.
Figure 8B:
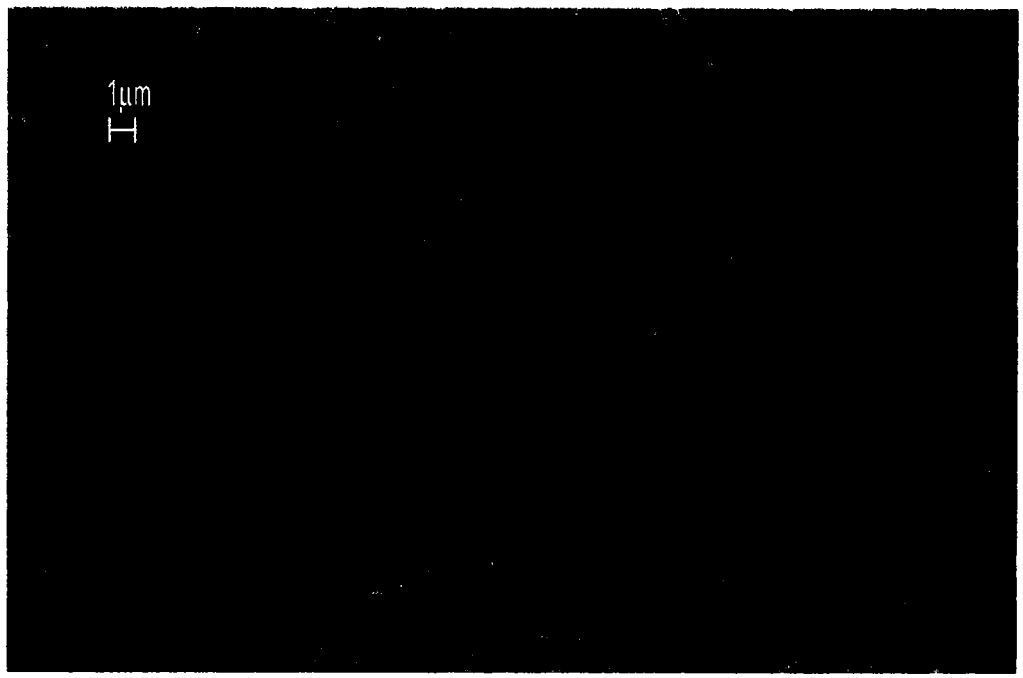

Morphological analysis of the gels confirmed the CS-MA and PEODA hydrogel pore structure suggested by the swelling and mechanical analysis. As suggested by the swelling and mechanical data, the CS-MA gels exhibited a larger pore structure compared to the PEODA gels both on the surface and in the interior (FIG. 6). The SEM morphological studies shown in FIGS. 6, 7, and 8 demonstrate a uniform pore structure, both on the surface and in the interior of the gels. The reproducibility (low standard deviation) of the swelling and mechanical data also suggests that chondroitin sulfate is substituted and forms hydrogels in a uniform and consistent manner.

Chondroitinase ABC treatments for damaged cartilage tissue may promote coverage of defects by repair cells and functional integration at defect edges. For example, CS-MA gels that are incubated in buffer without chondroitinase ABC do degrade compared with the CS-MA gels incubated with enzyme that completely degraded within one day (FIG. 9a). There may also be a dose response relationship between degradation and enzyme concentration. FIG. 9b demonstrates an increase in degraded disaccharide, as measured by absorbance, with increasing concentration of chondroitinase, with minimal degradation without the enzyme.

Figure 11A:
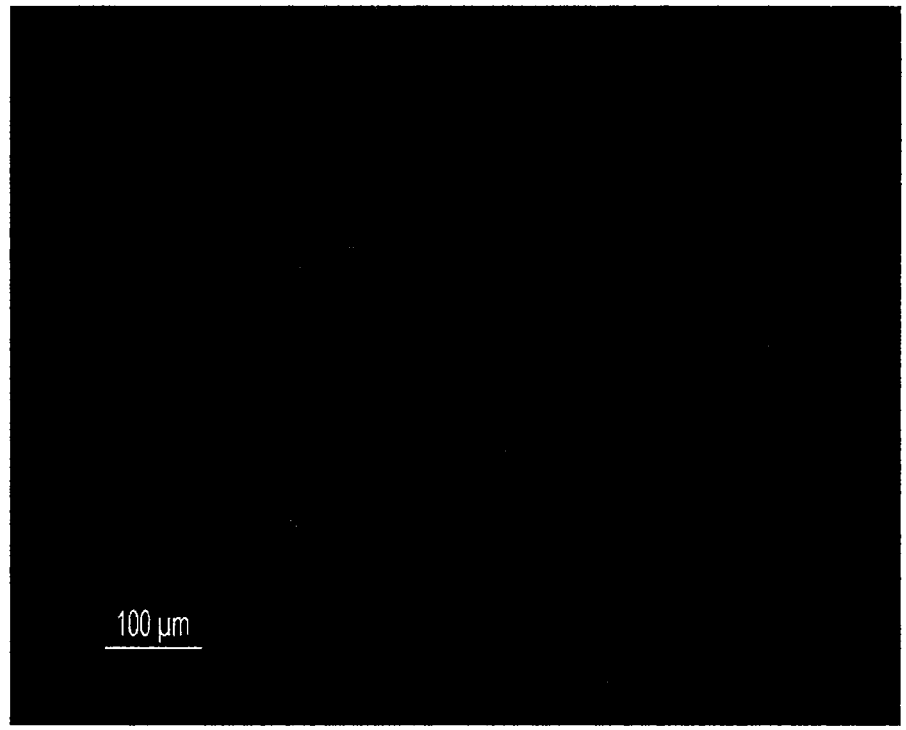
FIG. 11 is an image depicting of encapsulation one day after chondrocyte photoencapsulation: (A) Live/dead assay for visualization of viable cells and dead cells (original magnification 10×), (B) MTT staining for cells with mitochondrial metabolic activity (dark) (original magnification 10×).
Figure 11B:
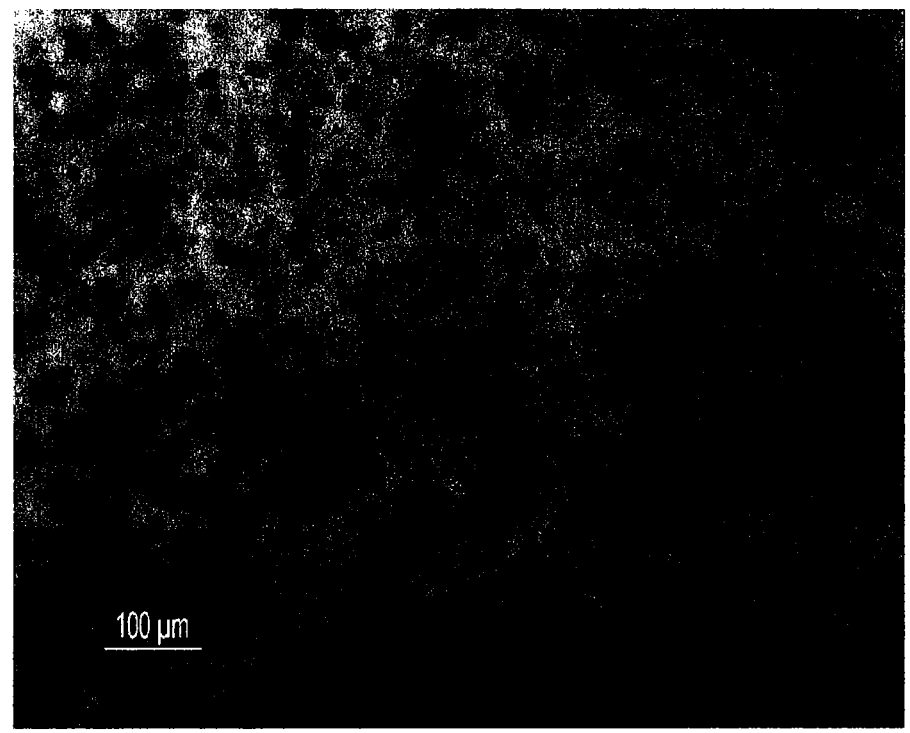

Cytotoxicity of the biopolymer scaffold system may be evaluated with chondrocytes, the cells that comprise cartilage, by, for example, using a Live-Dead fluorescent cell assay and MTT, a compound that actively metabolizing cells convert from yellow to purple. FIG. 11a pictures a majority of viable cells that are also actively metabolizing MIT (FIG. 11b).

Biologically Active Agents and Subject Compositions

In one aspect of this invention, a composition comprising a cross-linked polymer matrix or gel and one or more biologically active agents may be prepared. The biologically active agent may vary widely with the intended purpose for the composition. The term "biologically active agent" is art-recognized and refers to any chemical moiety that is a biologically, physiologically, or pharmacologically active substance that acts locally or systemically in a subject. Examples of biologically active agents, that may be referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released from the subject composition, for example, into adjacent tissues or fluids upon administration to a subject. In some embodiments, a biologically active agent may be used in cross-linked polymer matrix of this invention, to, for example, promote wound healing or cartilage formation. In other embodiments, a biologically active agent may be used in cross-linked polymer matrix of this invention, to treat, ameriolate, inhibit, or prevent a disease or symptom, in conduction with, for example, promoting wound healing or cartilage formation.

Further examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5% 10%, 20%, 30%, 40%, 50%, 60% or 70%, of a biologically active agent.

Non-limiting examples of biologically active agents include the following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheals, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, antianginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, humoral agents, hyperglycemic agents, hypnotics, hypoglycemic agents, ion exchange resins, laxatives, mineral supplements, miotics, mucolytic agents, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and pro-drugs.

Specific examples of useful biologically active agents from the above categories include: (a) anti-neoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoophedrine hydrochloride, and ephedrine; (e) various alkaloids such as codeine phosphate, codeine sulfate, and morphine; (f) mineral supplements such as potassium chloride, zinc chloride, calcium carbonate, magnesium oxide, and other alkali metal and alkaline earth metal salts; (g) ion exchange resins such as cholestyramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as antifungals, anti-virals, antiseptics and antibiotics; and (m) desensitizing agents and antigenic materials, such as those useful for vaccine applications.

More specifically, non-limiting examples of useful biologically active agents include the following therapeutic categories: analgesics, such as nonsteroidal anti-inflammatory drugs, opiate agonists and salicylates; antihistamines, such as H1-blockers and H2-blockers; anti-infective agents, such as antihelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as allylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, β-blocker sympatholytics, sympathomimetics, and adrenergic agonist sympathomimotics; cardiovascular agents, such as antianginals, β-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensives, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, β-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Other classes of biologically active agents from the above categories include: (1) analgesics in general, such as lidocaine, other caine analgesics or derivatives thereof, and nonsteroidal anti-inflammatory drugs (NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous β-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, other taxane derivatives, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) α-blocker sympatholytics, such as prazosin; (34) β-blocker sympatholytics, such as atenolol; (35) adrenergic agonist sympathomimetics, such as albuterol and dobutamine; (36) cardiovascular agents, such as aspirin (ASA) (enteric coated ASA); (37) β-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) β-blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifuigal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) H2-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin; (80) throinbolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkinsonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D compounds, such as calcitriol.

Further, recombinant or cell-derived proteins may be used, such as: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; recombinant human growth hormone (r-hGH); recombinant EPO (r-EPO); gene-activated EPO (GA-EPO); recombinant human hemoglobin (r-Hb); recombinant human mecasermin (r-IGF-1); recombinant interferon beta-la; lenograstim (G-CSF); olanzapine; recombinant thyroid stimulating hormone (r-TSH); and topotecan.

Still further, the following listing of peptides, proteins, and other large molecules may also be used, such as interleukins 1 through 18, including mutants and analogues; interferons α, γ, and β; chondrocytes, which may be useful for cartilage regeneration, luteinizing hormone releasing hormone (LHRH) and analogues, gonadatropin releasing hormone (GnRH), transforming growth factor (TGF); fibroblast growth factor (FGF); tumor necrosis factor-α & γ (TNF-α and γ); nerve growth factor (NGF); growth hormone releasing factor (GHRF), epidermal growth factor (EGF), connective tissue activated peptides (CTAPs), osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-α-1; γ-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, may be incorporated in a polymer matrix of the present invention. Members of the TGF supergene family include TGF-β, the beta transforming growth factors (for example, TGP-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)), Inhibins (for example, Inhibin A, Inhibin B), growth differentiating factors (for example, GDF-1); and Activins (for example, Activin A, Acivin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Various forms of the biologically active agents may be used. These include, without limitation, such forms as uncharged molecules, molecular complexes, salts, ethers, esters, amides, and the like, which are biologically activated when implanted, injected or otherwise placed into a subject.

In certain embodiments, other materials may be incorporated into subject compositions in addition to one or more biologically active agents. For example, plasticizers and stabilizing agents known in the art may be incorporated in compositions of the present invention. In certain embodiments, additives such as plasticizers and stabilizing agents are selected for their biocompatibility.

A composition of this invention may further contain one or more adjuvant substances, such as fillers, thickening agents or the like. In other embodiments, materials that serve as adjuvants may be associated with the composition. Such additional materials may affect the characteristics of the composition that results. For example, fillers, such as bovine serum albumin (BSA) or mouse serum albumin (MSA), may be associated with the polymer composition. In certain embodiments, the amount of filler may range from about 0.1 to about 50% or more by weight of the composition, or about 2.5, 5, 10, 25, 40 percent. Incorporation of such fillers may affect the sustained release rate of any encapsulated substance. Other fillers known to those of skill in the art, such as carbohydrates, sugars, starches, saccharides, celluloses and polysaccharides, including mannitose and sucrose, may be used in certain embodiments in the present invention.

Buffers, acids and bases may be incorporated in the compositions to adjust their pH. Agents to increase the diffusion distance of agents released from the composition may also be included.

The charge, lipophilicity or hydrophilicity of any subject composition may be modified by employing an additive. For example, surfactants may be used to enhance miscibility of poorly miscible liquids. Examples of suitable surfactants include dextran, polysorbates, and sodium lauryl sulfate. In general, surfactants are used in low concentrations, generally less than about 5%.

Biologically active agents may be incorporated into the cross-linked synthetic polymer composition by admixture. Alternatively, the agents may be incorporated into the cross-linked polymer matrix by binding these agents to the functional groups on the synthetic polymers. Such compositions may include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the cross-linked polymer composition involves mixing the active agent with a polyelectrophilic component prior to addition of the polynucleophilic component. By varying the relative molar amounts of the different components of the reactive composition, it is possible to alter the net charge of the resulting cross-linked polymer composition, in order to prepare a matrix for the delivery of a charged compound such as a protein or ionizable drug. As such, the delivery of charged proteins or drugs, which would normally diffuse rapidly out of a neutral carrier matrix, car be controlled.

For example, if a molar excess of a component that is polynucleophilic is used, the resulting matrix may have a net positive charge and can be used to ionically bind and deliver negatively charged compounds. Examples of negatively charged compounds that can be delivered from these matrices include various drugs, cells, proteins, and polysaccharides.

If a molar excess of a component that is polyelectrophilic is used, the resulting matrix has a net negative charge and can be used to ionically bind and deliver positively charged compounds. Examples of positively charged compounds that can be delivered from these matrices include various drugs, cells, proteins, and polysaccharides.

The cross-linked polymer matrix compositions of the present invention can also be used to deliver various types of living cells or genes to a desired site of administration in order to form new tissue. The term "genes" as used herein is intended to encompass genetic material from natural sources, synthetic nucleic acids, DNA, antisense-DNA and RNA.

For example, mesenchymal stem cells can be delivered using polymer matrices to produce cells of the same type as the tissue into which they are delivered. Mesenchymal stem cells may not differentiated and therefore may differentiate to form various types of new cells due to the presence of an active agent or the effects (chemical, physical, etc.) of the local tissue environment. Examples of mesenchymal stem cells include osteoblasts, chondrocytes, and fibroblasts. For example, osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

The cells or genes may be either allogeneic or xenogeneic in origin. For example, the compositions can be used to deliver cells or genes from other species that have been genetically modified. In some embodiments, the compositions of the invention may not easily be degraded in vivo, cells and genes entrapped within the cross-linked polymer matrix compositions will be isolated from the patient's own cells and, as such, will not provoke an immune response in the patient.

In order to entrap the cells or genes within a cross-linked polymer matrix, the cells or genes may, for example be premixed with a composition comprising functionalized chrondoitin sulfate, and optionally a further biocompatible polymer, and then a polymerizing agent is applied to the mixture to form a crosslinked polymer matrix, thereby entrapping the cells or genes within the matrix.

Repair or Replacement of Damaged Tissue

The compositions disclosed herein may be used in any number of tissue repair applications, such as, but not limited to, seroma and hematoma prevention, skin and muscle flap attachment, repair and prevention of endoleaks, aortic dissection repair, lung volume reduction, neural tube repair and the making of microvasuclar and neural anastomoses. Further, compositions of the invention may be used as an adhesive composition in the repair of damaged tissue.

In one embodiment, the repair of damaged tissue may be carried out within the context of any standard surgical process allowing access to and repair of the tissue, including open surgery and laparoscopic techniques. Once the damaged tissue is accessed, a composition of the invention is placed in contact with the damaged tissue along with any surgically acceptable patch or implant, if needed. When used to repair lacerated or separated tissue, such as by joining two or more tissue surfaces, the composition may be applied to one or more of the tissue surfaces and then the surfaces are placed in contact with each other and adhesion occurs therebetween.

When used to repair herniated tissue, a surgically acceptable patch can be attached to the area of tissue surrounding the herniated tissue so as to cover the herniated area, thereby reinforcing the damaged tissue and repairing the defect. When attaching the patch to the surrounding tissue, a composition of the invention may be applied to either the patch, to the surrounding tissue, or to the patch after the patch has been placed on the herniated tissue. Once the patch and tissue are brought into contact with each other, adhesion may occur therebetween.

In an embodiment, substantially all reactive components of a composition of the invention are first mixed, then delivered to the desired tissue or surface before substantial cross-linking, for example by electromagnetic radiation, has occurred. The surface or tissue to which the composition has been applied may then contacted with the remaining surface, i.e. another tissue surface or implant surface, preferably immediately, to effect adhesion.

The surfaces to be adhered may be held together manually, or using other appropriate means, while the cross-linking reaction is proceeding to completion. Cross-linking is may typically sufficiently complete for adhesion to occur within about 5 to 60 seconds after mixing the components of the adhesive composition. However, the time required for complete cross-linking to occur is dependent on a number of factors, including the type and molecular weight of each reactive component, the degree of functionalization, and the concentration of the components in the cross-linkable compositions (e.g., higher component concentrations result in faster cross-linking times).

Thus, in one embodiment the compositions of the present invention are delivered to the site of administration using an apparatus that allows the components to be delivered separately. Such delivery systems may involve a multi-compartment spray device. Alternatively, the components can be delivered separately using any type of controllable extrusion system, or they can be delivered manually in the form of separate pastes, liquids or dry powders, and mixed together manually at the site of administration. Many devices that are adapted for delivery of multi-component tissue sealants/hemostatic agents are well known in the art and can also be used in the practice of the present invention.

Yet another way of delivering the compositions of the present invention is to prepare the reactive components in inactive form as either a liquid or powder. Such compositions can then be activated after application to the tissue site, or immediately beforehand, by applying an activator. In one embodiment, the activator is a buffer solution having a pH that will activate the composition once mixed therewith. Still another way of delivering the compositions is to prepare preformed sheets, and apply the sheets as such to the site of administration. One of skill in the art can easily determine the appropriate administration protocol to use with any particular composition having a known gel strength and gelation time The compositions described herein can be used for medical conditions that require a coating or sealing layer to prevent the leakage of gases, liquid or solids. The method entails applying both components to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid. These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material. In addition, the compositions can be used to fill spaces in soft and hard tissues that are created by disease or surgery.

For example, polymer matrix compositions of the invention can be used to block or fill various lumens and voids in the body of a mammalian subject. The compositions can also be used as biosealants to seal fissures or crevices within a tissue or structure (such as a vessel), or junctures between adjacent tissues or structures, to prevent leakage of blood or other biological fluids.

The compositions can also be used as a large space-filling device for organ displacement in a body cavity during surgical or radiation procedures, for example, to protect the intestines during a planned course of radiation to the pelvis.

The compositions of the invention can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the reaction mixture is preferably applied to the interior surface of the vessel (for example, via catheter) immediately following mixing of the first and second synthetic polymers. Because the compositions of the invention are not readily degradable in vivo, the potential for restenosis due to degradation of the coating is minimized.

The compositions of the invention can also be used for augmentation of soft or hard tissue within the body of a mammalian subject. Examples of soft tissue augmentation applications include sphincter (e.g., urinary, anal, esophageal) augmentation and the treatment of rhytids and scars.

Examples of hard tissue augmentation applications include the repair and/or replacement of bone and/or cartilaginous tissue.

The compositions of the invention may be used as a replacement material for synovial fluid in osteoarthritic joints. The compositions may reduce joint pain and improve joint function by restoring a soft gel network in the joint. The crosslinked polymer compositions can also be used as a replacement material for the nucleus pulposus of a damaged intervertebral disk. The nucleus pulposus of the damaged disk is first removed, and the reactive composition is then injected or otherwise introduced into the center of the disk. The composition may either be cross-linked prior to introduction into the disk, or allowed to cross-link in situ.

In some embodiments, one, two, or more polymerizing agents may be used. For example, electromagnetic radiation may be used alone, or together with a photoinitiator. A photoinitiator alone may be used. Additionally or independently, a redox polymerizing agent may be used. The electromagnetic radiation, or a photoinitiator may trigger a fast polymerization. Such fast polymerization may ensure that the composition remains in the desired location. A redox polymerizing agent may be used simultaneously, before, or after electromagnetic radiation. A redox polymerizing agent may trigger a slow polymerization, for example, about 2 hours.

In a general method for effecting augmentation of tissue or a disk within the body of a mammalian subject, the components of the reactive composition are injected, implanted, or infused simultaneously to a tissue or disk site in need of augmentation. The present invention may be prepared to include an appropriate vehicle for this injection, implantation, infusion or direction. Once inside the patient's body, the functionalized chondroitin sulfate and, for example, a compound comprising an amine group may react with each other to form a crosslinked polymer network in situ. The functionalized chrondrotin sulfate may also react with primary amino groups on, for example, lysine residues of collagen molecules within the patient's own tissue, providing for "biological anchoring" of the compositions with the host tissue.

The polymer matrix, alternatively, may be formed as a solid object implantable in the anatomic area, or as a film or mesh that may be used to cover a segment of the area. A variety of techniques for implanting solid objects in relevant anatomic areas will be likewise familiar to practitioners of ordinary skill in the art.

In some embodiments, compositions disclosed herein may be positioned in a surgically created defect that is to be reconstructed, and is to be left in this position after the reconstruction has been carried out. The present invention may be suitable for use with local tissue reconstructions, pedicle flap reconstructions or free flap reconstructions.

Assays and Kits

In some embodiments, this invention is directed to assays and kits for assessing effectiveness and diagnosis of cartilage degradation diseases such as arthritis. In some embodiments, the assay or kits detect the presence of enzymes that may degrade a cross-linked polymer matrix of this disclosure.

Osteoarthritis, for example is a degenerative disease of the articulating cartilages of joints. In its early stages it may be largely non-inflammatory, and may be distinct from rheumatoid arthritis. Osteoarthritis may not be a single disease but may be indicative of joint failure that may result from various factors (e.g. genetic predisposition, mechanical overusage, joint malformation or a prior injury, etc.). Destruction of joint articular cartilage is the central progressive feature of osteoarthritis. Other diseases in which joint cartilage may be destroyed include: rheumatoid arthritis, juvenile rheumatoid arthritis, ankylosing spondylitis, psoriatic arthritis, Reiter's syndrome, relapsing polychondritis, the low back pain syndrome, and other infectious forms of arthritis. In general, arthritis is associated with cartilage degrading activity.

The assays, methods and kits disclosed herein may be used to detect early evidence of accelerated cartilage degradation in mildly symptomatic patients, to monitor disease progress in more advanced patients, and as a means of monitoring the effects of drugs or other therapies. In other embodiments, this invention contemplates a kit including subject compositions and cross-linked polymer matrices, and optionally instructions for their use. Uses for such kits include, for example, therapeutic applications. The invention further provides kits for use in treating a disease or condition. For example, the kit may comprise a subject functionalized chondroitin sulfate compound and a biocompatible polymer or an compound comprising an amine moiety, either already combined or provided separately.

Test kits for use may include cross-linked matrix polymers comprising functionalized disaccharides that degrade in the presence of cartilage degrading enzymes, for example, chondroitinase and collagenase. Other proteases and enzymes may be detected using such kits.

EXEMPLIFICATION

The invention now being generally described, it will be more readily understood by reference to the following examples which are included merely for purposes of illustration of certain aspects and embodiments of the present invention, and are not intended to limit the invention.

Example 1

Materials

Chondroitin sulfate A sodium salt (CS, Type A 70%, balanced with Type C from bovine trachea) and Acetone (<0.5% water) is obtained from SIGMA, MO. Glycidyl methacrylate (GMA, 98% purity) is obtained from Polysciences, PA. Acrylate-PEG-Acrylate (PEODA, 100% M 3127, Polydispersity=1.03, as determined by GPC analysis) is obtained from Shearwater, Ala. Phosphate saline buffer (PBS, pH7.4) may be obtained from GIBCO.

Example 2

Synthesis of GMA-CS 10 g CS is dissolved in 100 ml PBS, followed by addition of 10 ml GMA, while vigorously stirring at room temperature. Samples are collected at Days 1, 3, 5, 7, 10 and 15 by acetone precipitation and purified twice by acetone extraction. The GMA-CS products (Day 1, 3, 5, 7, 10 and 15) are lyophilized for 24 hrs and stored at 4° C.

Example 3

Synthesis of Aldehyde Functionalized CS and Cross-Linked Matrix

Six hundred mg of chondroitin sulfate Type A (0.8~1.2 mmol of adjacent diol, 70% CS-A, Sigma) and 616 mg of sodium periodate (~2.88 mmol, $NaIO_4$, Sigma) are dissolved together in 10 ml of de-ionized water and protected from light. The reaction is allowed to continue for ~14 hr in dark with vigorous stirring. The insoluble byproducts are removed with 0.22 μm filter and the product is loaded into a Sephedex G-25 (Sigma) size exclusion chromatography (SEC) column, by which the product was purified from the water-soluble byproducts and un-reacted small molecules. The product, chondroitin sulfate-aldehyde (CS-ald), is obtained by lyophilization with a yield rate of ~90%. The determination of aldehyde substitution degree is performed via a hydroxylamine hydrochloride titration. The result is 60~70% substitution.

A tissue adhesive is formulated by mixing equal volumes (20 μl) of 25% CS-ald and 40% bovine serum albumin (BSA, Sigma). The adhesive is used immediately after the formulation and the reaction is completed in 2~5 min with the Schiff-base mechanism.

Example 4

NMR Methods

NMR spectra are recorded with a Unity Plus 500 MHz spectrometer (Varian Associates). For H-NMR in deuterium-d2 (D20, 99.9% h, SIGMA) approximately 50 mg material was dissolved in 1.0 ml $D_2O$, and $^2HOH$ at 4.8 ppm was used as the reference peak. For $^{13}$C-NMR in deuterium-$d_2$ ($D_2O$, 99.9% 2H, SIGMA) the pulse is 51.9 degrees, using a pulse length of 7 μs, acquisition time of 1.300 sec, and 80000 repetitions at 50° C.

Example 5

Photocrosslinking and Hydrogel Swelling Ratio

GMA-CS and PEODA are mixed 1:1 (w/w) and dissolved in water for a GMA-CS concentration of 10% (w/w). One hundred fifty liters of macromer solution (10% w/v)) are placed in tissue insert (diameter 8 mm) and polymerized. Photocrosslinking is initiated with a cytocompatible UV photoinitiator Ingracure 2959 (0.05% w/w, Ciba Geigy) and 365 nm light at ~10 mW/cm2 as measured by a radiometer. The macromers are photopolymerized for 30 min.

The photocross-linked hydrogels are equilibrated in PBS at 37° C. for 18 h. The water content of the hydrogels is determined by measuring the wet weight (Ww) of the constructs. Dry weight (Wd) of the hydrogels was measured after lyophilization for 24 h. The hydrogel equilibrated swelling ratio, q, is calculated by $q \approx Ww/Wd$.

Example 6

Rheological Characterization

PBS-equilibrated copolymerized CS-MA and poly(ethylene oxide)-diacrylate (PEODA) (3,400; Shearwater Polymers, Knoxville, Tenn.) macromers (20% w/v) hydrogel constructs are prepared in tissue culture inserts as previously described. The constructs average 13.21±0.86 mm in diameter and 4.67±0.16 mm in thickness as measured by current sensing micrometer. The weight percentage of PEODA and CS-MA in the constructs is varied from 0% (i.e., pure PEODA), 25%, 50%, 75% and 100% (i.e., pure CS-MA). Rheological tests are performed on a RFS-3 rheometer (Rheometric Scientific Inc.) using the parallel-plate configuration. The pilot dynamic shear strain-sweep test at a frequency 6.28 rad/s indicates a 0.1% shear strain that is in the linear stress-strain range for the samples with various concentration ratios, and such linearity is confirmed using the dynamic shear strain-sweep test for each test sample prior to the dynamic shear frequency-sweep test. The dynamic shear frequency-sweep is tested over a range of frequencies from 0.1 to 100 rad/s at a shear amplitude of 0.1%.

Example 7

Morphological Analysis

Hydrogel blocks synthesized from 20% (w/v) macromer solutions of CS-MA and PEODA were cut, frozen, and lyophilized. The surface and the cut edge of the hydrogels are analyzed on a LEO 1530 Field Emission scanning electron microscope (LEO Electron Microscopy Inc.).

Example 8

Degradation Experiments

Figure 9:
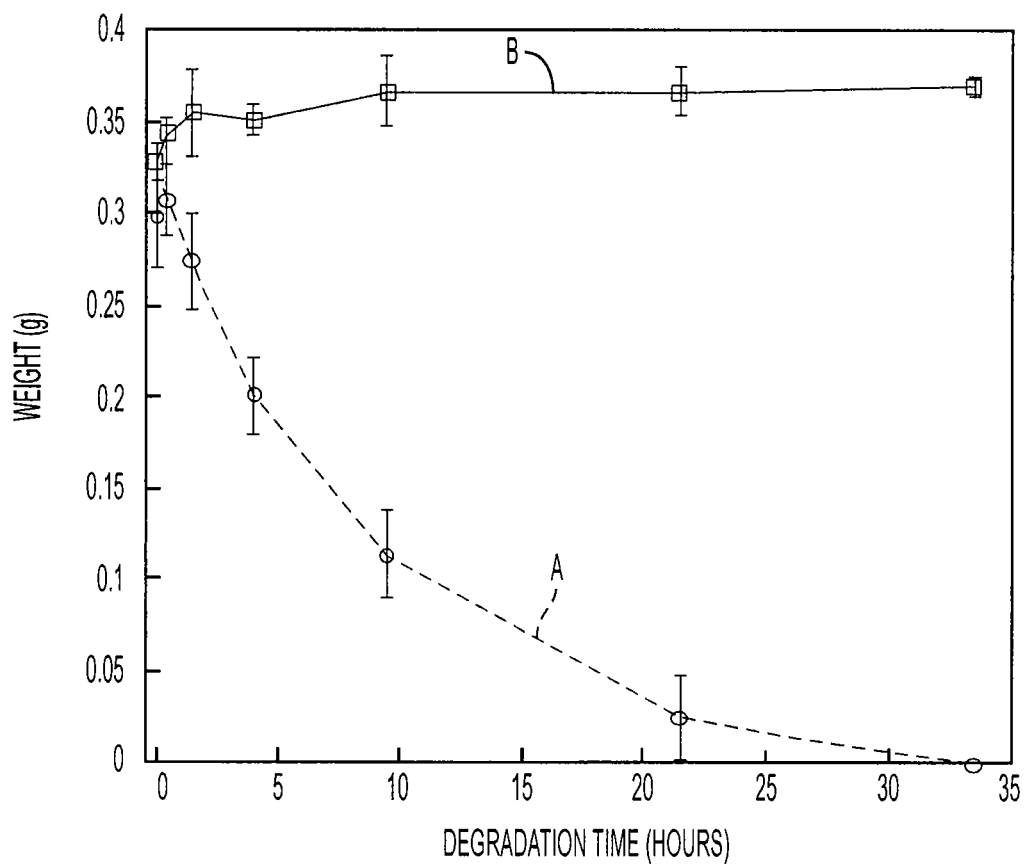
FIG. 9 is a line graph depicting the degradation profiles of 20% (w/v) CS-MA gels showing weight changes with degradation time in A: chondroitinase digestion buffer and B: no addition of chondroitinase.
Figure 10:
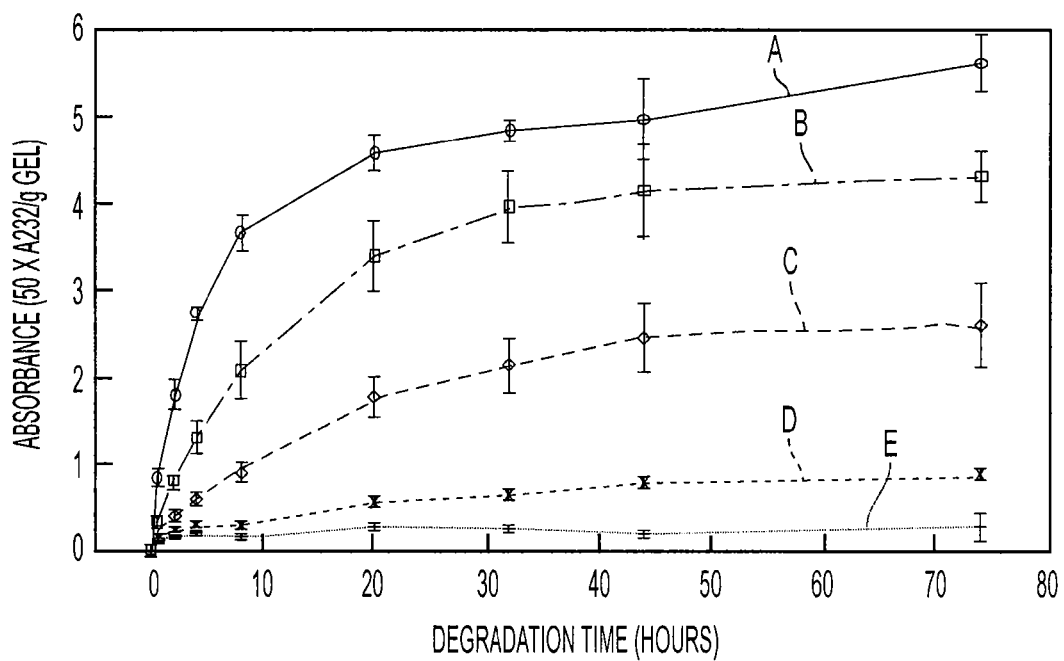
FIG. 10 is a line graph depicting changes with degradation time in light absorbance of digestion buffered solution of different enzyme concentration (A: 2.5 g/ml, B: 0.25 g/ml, C: 0.025 g/ml, D: 0.0025 g/ml and E: no addition of chondroitinase).

Degradation of the polymerized hydrogels is carried out in pH 8.0 Tris-HCl buffered digestion solution (Tris-HCl 60 mM/L, sodium acetate 40 mM/L and bovine serum albumin 1.5×10-4 mg/L) at 37° C., 5% CO2. Photopolymerized CS-MA hydrogels (20% w/v) are weighed and placed in 24-well cell culture plate with 2.5 ml digestion buffer with or without chondroitinase ABC (0.8 mg/ml). At specified time points, the weight of constructs are measured. Chondroitinase ABC concentration is also varied (0.0025 g/ml, 0.025 g/ml, 0.25 g/ml and 2.5 g/ml) and at specified time points, the absorbance of digestion solutions is measured at 232 nm with a background subtraction at 600 nm in order to monitor disaccharide evolution as degradation proceeded (n=3). Values are normalized to hydrogel construct original weight. FIG. 9 demonstrates the decrease in CS-MA gel weight over at 33 hours in the presence of chrondroitinase ABC. The gels are completely degraded by 33 hours in the presence of enzyme compared to control gels incubated without enzymes that maintain a constant weight throughout the experiment. Release of degraded chondroitin sulfate from the gels was measured in the buffer with varying concentrations of chrondoitinase enzyme. Increasing the enzyme concentration increases the concentration of degradation byproducts observed in the surrounding buffer.

Example 9

Cell Encapsulation and Viability

CS-MA and PEODA ar combined in a 1:1 ratio and dissolved in PBS with 100 U/ml penicillin G and 100 μg/ml streptomycin to from a 20% (w/v) solution. After addition of 0.05% Irgacure D-2959 (w/v), the macromer solutions are added to re-suspend the cell pellet to make a final concentration of $20 \times 10^6$ cells/ml, and subsequently photopolymerized for 8 min with 10 mW/cm$^2$ UV light. The constructs are then transferred and incubated in chondrocyte media high-glucose Dulbeccos modified Eagle's medium (DMEM), 10% fetal bovine serum (FBS), 10 μg/ml vitamin C, 12.5 mM HEPES, 0.1 mM nonessential amino acids and 0.4 mM proline] at 37° C., 5% $CO_2$.

MTT assay and live/dead staining assay are respectively performed to measure cell viability after 1 day in culture. For MT assay, the constructs are washed twice with PBS and 2 mls of MTT solution (0.5 mg/ml in DMEM with 2% FBS) are added to each well for 2-4 h. Actively metabolizing cells are observed by light microscopy. Cell viability of the encapsulated cells is also evaluated with Live/Dead Viability/Cytotoxicity Kit (Molecular Probes, Eugene, Oreg., U.S.A.). Thin slices (100-200 μm) of three layers are prepared with a surgical blade from the constructs. The slices are incubated for 30 minutes in Live/Dead assay reagents (2 μM calcein AM and 4 μM. Fluorescence microscopy is performed using a fluorescein optical filter (485±10 nm) for calcein AM and a rhodamine optical filter (530±12.5 nm) for Ethidium homodimer-1.

Example 10

IVD Applications

A polymer composition with 80% CSMA with 0.1% (w/v) Irgacure D2959 photoinitiator or a polymer composition with 50% CSMA/10% PEODA with 0.1% (w/v) Irgacure D2959 is used. Gels photopolymerized in a IVD space in part A are removed and the swelling ratio is determined. A water-soluble redox initiating system is used with CSMA that includes 0.1% D2959 and 0.15 M sodium persulfate-0.12M sodium thiosulfate. The system is implanted in cadaveric IVD space. After photopolymerization the cadaveric spine is be placed in a 37° C. incubator to allow the redox polymerization. After gelation, the gel size and water content is determined. Results obtained in this model are expected to correlate with in vivo results.

Example 11

Rabbit Studies

An IVD rabbit stab model is used to mimic the normal disc degeneration process. Animals are anesthetized with 50 mg/kg ketamine IM and 10 mg/kg xylazine IM and a stab wound is be created in the IVD disk space using an 18-gauge needle. Discs are allowed to degenerate for four weeks before polymer injection. The polymer formulation is injected into the disrupted disk space and polymerized. Control IVD disc spaces are injected with saline instead of polymer. Animals are monitored radiographically once a week to observe implant placement, disk height, and tissue degradation or inflammation. Animals are sacrificed after 4, 8 and 12 weeks and histological analysis is performed to observe polymer size and shape, inflammation, and surrounding tissue integration and repair.

EQUIVALENTS

Contemplated equivalents of the polymers, polymeric matrices, subunits and other compositions described herein include such materials which otherwise correspond thereto, and which have the same general properties thereof (e.g., biocompatible), wherein one or more simple variations of substituents are made which do not adversely affect the efficacy of such molecule or composition to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

Also incorporated by reference are the following:

Patents and Patent Applications

U.S. 2002/0022588, U.S. Pat. No. 6,605,294, U.S. Pat. No. 6,602,975, U.S. 2003/0119985, U.S. 2003/0031697

We claim:

1. A composition comprising a cross-linked polymer matrix, the cross-linked polymer matrix comprising functionalized chondroitin sulfate, wherein the functionalized chondroitin sulfate comprises at least 100 monomeric units, and at least one polymerizing moiety per about 10 monomeric units, wherein the polymerizing moiety is a methacrylate moiety, and wherein at least one monomeric unit of the functionalized chondroitin sulfate is cross-linked into the cross-linked polymer matrix.

2. The composition of claim 1, wherein said monomeric unit of chondroitin sulfate is functionalized with an aldehyde moiety.

3. The composition of claim 1, wherein said cross-linked polymer matrix is a hydrogel.

4. The composition of claim 1, further comprising a detectable agent.

5. The composition of claim 1, further comprising a biologically active agent.

6. The composition of claim 4, wherein said detectable agent is a dye.

7. The composition of claim 6 wherein said dye is a fluorescent agent.

8. The composition of claim 5, wherein said biologically active agent is a chondrocyte.

9. The composition of claim 5, wherein said biologically active agent is a mesenchymal stem cell.

10. The composition of claim 1, wherein said cross-linked polymer matrix further comprises at least one monomeric unit of a biocompatible polymer.

11. The composition of claim 1, wherein said cross-linked polymer matrix further comprises a compound comprising an amine moiety.

12. The composition of claim 11, wherein said compound is a protein.

13. The composition of claim 11, wherein said compound is albumin.

14. The composition of claim 10, wherein said biocompatible polymer is poly(ethylene glycol).

15. The composition of claim 10, wherein said cross-linked polymer matrix by weight comprises at least 75% of said biocompatible polymer by weight.

16. The composition of claim 10, wherein said cross-linked polymer matrix by weight comprises at least 50% of said biocompatible polymer by weight.

17. The composition of claim 10, wherein said cross-linked polymer matrix by weight comprises at least 25% of said biocompatible polymer by weight.

18. The composition of claim 1, wherein said functionalized chondroitin sulfate is functionalized with an aldehyde moiety and a methacrylate moiety.

\* \* \* \* \*